(12) United States Patent
Lee et al.

(10) Patent No.: US 9,482,680 B2
(45) Date of Patent: Nov. 1, 2016

(54) TEST PLATFORM, TEST APPARATUS AND CONTROL METHOD THEREOF

(71) Applicant: SAMSUNG ELECTRONICS CO., LTD., Suwon-si (KR)

(72) Inventors: Ki Ju Lee, Suwon-si (KR); Suk Yong Lee, Suwon-si (KR); Young Goun Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 10 days.

(21) Appl. No.: 13/949,674

(22) Filed: Jul. 24, 2013

(65) Prior Publication Data

US 2014/0048591 A1 Feb. 20, 2014

(30) Foreign Application Priority Data

Aug. 17, 2012 (KR) .................. 10-2012-0090346

(51) Int. Cl.
*G01N 35/00* (2006.01)

(52) U.S. Cl.
CPC ........ *G01N 35/00* (2013.01); *G01N 35/00069* (2013.01); *G01N 35/00693* (2013.01)

(58) Field of Classification Search
CPC ........... G01N 35/00; G01N 35/00069; G01N 35/00693; G06F 17/30; G06F 17/30725; G06F 17/30879; G06K 19/00; G06Q 10/08; G06Q 10/087; G06Q 20/1085; G06Q 30/02; G06Q 30/06; G06Q 50/22

See application file for complete search history.

(56) References Cited

U.S. PATENT DOCUMENTS

| | | | | |
|---|---|---|---|---|
| 5,397,709 | A * | 3/1995 | Berndt | G01N 21/253 356/442 |
| 6,327,031 | B1 | 12/2001 | Gordon | |
| 2003/0104486 | A1 | 6/2003 | Selvan | |
| 2003/0133840 | A1 | 7/2003 | Coombs et al. | |
| 2004/0067055 | A1 * | 4/2004 | Kiening | 396/563 |
| 2008/0217246 | A1 * | 9/2008 | Benn | G01N 35/00029 210/645 |
| 2010/0312574 | A1 | 12/2010 | Yoo | |
| 2011/0014094 | A1 * | 1/2011 | Kim | B01L 3/5027 422/400 |
| 2011/0104009 | A1 | 5/2011 | Kawamura et al. | |

OTHER PUBLICATIONS

Communication dated Dec. 2, 2013 issued by the European Patent Office in counterpart European Patent Application No. 13176478.9.

* cited by examiner

*Primary Examiner* — Sonji Johnson
(74) *Attorney, Agent, or Firm* — Sughrue Mion, PLLC

(57) ABSTRACT

A test platform is provided for testing a detection module of a test apparatus to determine whether correction is needed or for quality control of the test apparatus. The test platform includes a body, and at least one reference material which is formed on the body and on which at least one color is printed.

25 Claims, 23 Drawing Sheets

TEST PLATFORM, TEST APPARATUS AND CONTROL METHOD THEREOF

CROSS-REFERENCE TO RELATED APPLICATION

This application claims priority from Korean Patent Application No. 2012-0090346, filed on Aug. 17, 2012 in the Korean Intellectual Property Office, the disclosure of which is incorporated herein by reference.

BACKGROUND

1. Field

Apparatuses and methods consistent with exemplary embodiments relate to a test apparatus for testing a biosubstance through a microfluidic device, and a test platform used for quality control and correction of the test apparatus.

2. Description of the Related Art

A microfluidic device is used to manipulate a small quantity of fluid to cause a biological or chemical reaction.

In general, a microfluidic structure that performs an independent function in a microfluidic device may include a chamber for accommodating a fluid therein, a channel through which the fluid flows, and a structure for adjusting flow of the fluid. A device constructed to perform predetermined processing steps and manipulations by providing such a microfluidic structure on a substrate in the form of a chip in order to perform various tests including an immune serum reaction, a biochemical reaction, etc. on a small chip is called a lab-on-a chip.

In order to transfer a fluid in a microfluidic structure, driving pressure is needed. The driving pressure may be capillary pressure or pressure by a pump. Recently, a disc type microfluidic device of performing a series of processes by providing a microfluidic structure on a disc-shaped platform and moving a fluid using a centrifugal force has been developed. Such a disc type microfluidic device is called a lab compact disc (CD) or a lab-on-a disc.

The microfluidic device may include a chamber for detecting a substance to be analyzed or tested, or a detection target such as a reactor.

A test apparatus may include a light source, a light receiver for detecting the detection target of the microfluidic device, and a blood tester for detecting results of biochemical reactions that occur in the detection target.

SUMMARY

One or more exemplary embodiments provide a test platform for testing a detection module of a test apparatus to determine whether correction is needed or for quality control of the test apparatus, the test platform including a reference material on which colors for testing the detection module are printed.

One or more exemplary embodiments also provide a test apparatus for using a test platform to determine whether correction of a detection module is needed and for quality control.

In accordance with an aspect of an exemplary embodiment, there is provided a test platform including: a body; and at least one reference material which is formed on the body and on which one or more colors are printed.

The colors may be different from each other in at least one of printed shape, brightness, and thickness.

The test platform may further include a tag storing information related to the test platform.

The tag may be formed on the body, and include a barcode, a QR code, or an RFID tag.

The tag may include identification information for identifying the test platform, and a reference value to be used in testing a test apparatus.

The reference value may be a reference value with respect to the result of detection regarding the reference material by the test apparatus, and include a reference range set in advance for each reference material.

The test platform may further include an accommodating unit configured to accommodate the at least one reference material therein.

The test platform may further include a plurality of magnetic substances disposed adjacent to the at least one reference material and the tag.

The reference material may be formed by attaching a print film on which one or more colors are printed on a reactor.

The body may be in the shape of a disc.

In accordance with an aspect of another exemplary embodiment, there is provided a test apparatus including: a light source configured to irradiate light to a test platform including a tag and a reference material; a detection module configured to read information stored in the tag of the test platform, the detection module including a light receiver configured to face the light source and to receive the light irradiated by the light source and passed through the reference material to detect the reference material when reference material of the test platform is interposed between the light receiver and the light source; and a controller configured to compare a reference value included in the information read from the tag and a result of the detection of the reference material by the detection module, and to determine whether the detection module needs to be corrected based on a result of the comparison.

The test apparatus may further include: a rotation driver configured to rotate the test platform; and a detection module driver configured to move the detection module in a radial direction, wherein the controller controls the detection module driver to move the detection module in the radial direction until the light receiver of the detection module is positioned at a location corresponding to a radial distance at which the tag or the reference material is positioned, and controls the rotation driver to rotate the test platform until the tag or the reference material faces the light receiver.

The light source may be an area light source including a backlight unit.

The light receiver may include a CCD image sensor or a CMOS image sensor.

The test platform may include a plurality of magnetic substances disposed adjacent to the tag and the reference material, and the detection module may include a plurality of magnets for applying an attraction force to the magnetic substances so that the tag and the reference material are stopped at locations at which the tag and the reference material face the light receiver.

The controller may control the detection module driver to move the detection module in a radial direction until the magnets of the detection module are positioned at locations corresponding to radial distances at which the magnetic substances of the test platform are positioned, and controls the rotation driver to rotate the test platform until the magnetic substances of the test platform face the magnets of the detection module.

The controller may receive identification information for identifying the test platform, and a reference value to be used in testing the detection module, from the light receiver of the detection module, wherein the light receiver acquires the identification information and the reference value by reading the tag, identify that the corresponding platform is a test platform for testing the detection module, based on the identification information, receive, if the light receiver of the detection module detects light passed through one or more colors printed on the reference material, the result of the detection, compare the result of the detection to the reference value, and correct the light receiver of the detection module if the result of the detection is not identical to the reference value.

The reference value may be a reference value with respect to the result of detection regarding the reference material by the light receiver of the detection module, and include a reference range set in advance for each reference material.

the controller may correct, if the result of the detection is not identical to the reference value, a detection condition of the light receiver such that the result of the detection by the light receiver is identical to the reference value, and after the detection condition of the light receiver is corrected, the controller may control the light receiver to again detect light passed through one or more colors printed on the reference material, and determine whether the result of the detection is identical to the reference value.

In accordance with an aspect of another exemplary embodiment, there is provided a method of controlling a test apparatus including: receiving information stored in a tag of a test platform, the information including a reference value to be used in testing a detection module of the test apparatus; comparing the reference value to a result of a detection of light passed through a reference material by the detection module; and correcting a light receiver of the detection module if the result of the detection is not identical to the reference value.

The receiving of the information including the reference value may include: moving the detection module in a radial direction until the light receiver of the detection module is positioned at a location corresponding to a radius distance at which the tag is positioned; rotating the test platform until the tag faces the light receiver; receiving identification information for identifying the test platform, and a reference value to be used in testing the detection module, from the light receiver, wherein the light receiver acquires the identification information and the reference value by reading the tag, and storing the identification information and the reference value; and identifying that the corresponding platform is a test platform for testing the detection module based on the identification information.

The test platform may include a magnetic substance disposed adjacent to the tag, the detection module may include a magnet for applying an attraction force to the magnetic substance so that the tag is stopped at a location at which the tag faces the light receiver, and the moving the detection module in the radial direction may include moving the detection module in the radial direction until the magnet of the detection module arrives at a location corresponding to a radial distance at which the magnetic substance disposed adjacent to the tag of the test platform is positioned.

The rotating the test platform may include rotating the test platform so that the magnetic substance of the test platform faces the magnet of the detection module when the magnet of the detection module is positioned at a location corresponding to a radial distance at which the magnetic substance disposed adjacent to the tag of the test platform is positioned, The comparing of the result of the detection to the reference value may include: moving the detection module in a radial direction until the light receiver of the detection module arrives at a location corresponding to a radial distance at which the reference material is positioned; rotating the test platform until the reference material faces the light receiver; and receiving, if the light receiver detects light passed through one or more colors printed on the reference material, the result of the detection from the light receiver, and comparing the result of the detection to the reference value.

The test platform may include a magnetic substance disposed adjacent to the reference material, the detection module may include a magnet for applying an attraction force to the magnetic substance so that the magnetic substance is stopped at a location at which the reference material faces the light receiver, and the moving the detection module in the radial direction may include moving the detection module in the radial direction until the magnet of the detection module arrives at a location corresponding to a radial distance at which the magnetic substance disposed adjacent to the reference material of the test platform is positioned.

The rotating the test platform may include rotating the test platform so that the magnetic substance of the test platform faces the magnet of the detection module when the magnet of the detection module is positioned at a location corresponding to a radial distance at which the magnetic substance disposed adjacent to the reference material of the test platform is positioned.

The correcting of the light receiver of the detection module if the result of the detection is not identical to the reference value may include: correcting, if the result of the detection is not identical to the reference value, a detection condition of the light receiver such that the result of detection by the light receiver is identical to the reference value, and after the detection condition of the light receiver is corrected, controlling the light receiver to again detect light passed through one or more colors printed on the reference material, and determining whether the result of the detection is identical to the reference value.

BRIEF DESCRIPTION OF THE DRAWINGS

The and/or other aspects will become apparent and more readily appreciated from the following description of exemplary embodiments, taken in conjunction with the accompanying drawings of which.

DETAILED DESCRIPTION

Figure 1:
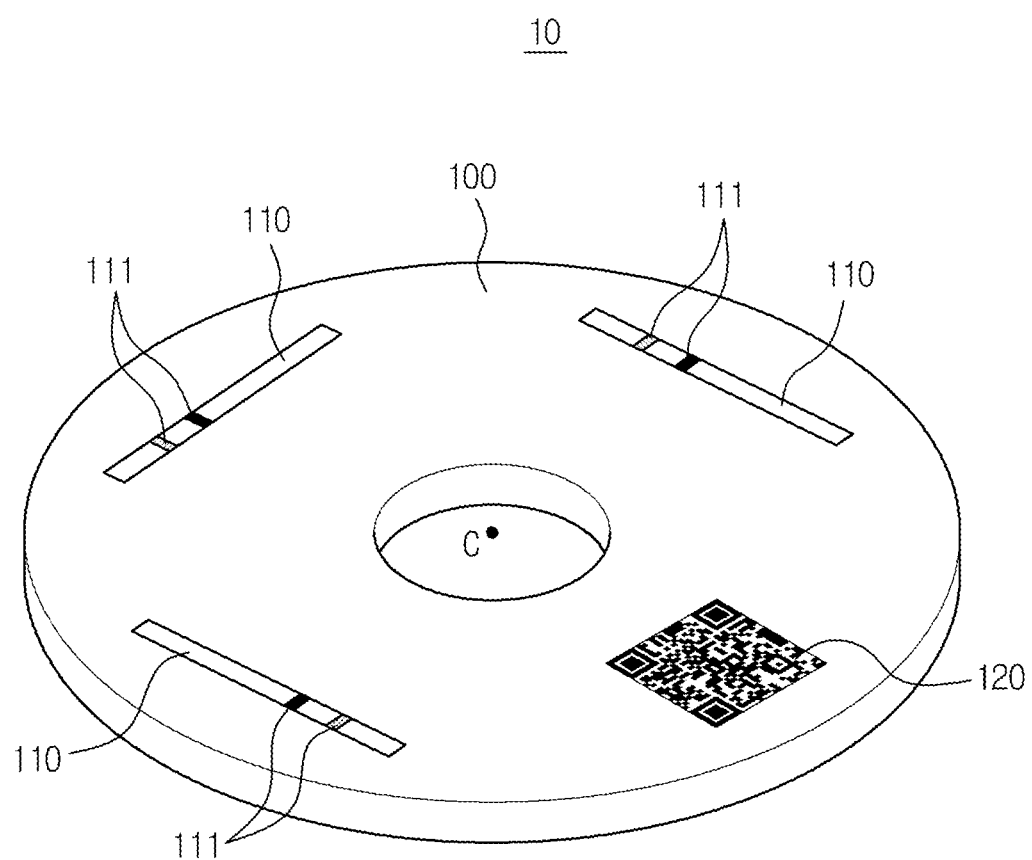
FIG. 1 schematically shows the configuration of a test platform in accordance with an exemplary embodiment.

Reference will now be made in detail to exemplary embodiments, examples of which are illustrated in the accompanying drawings, wherein like reference numerals refer to like elements throughout.

Figure 2:
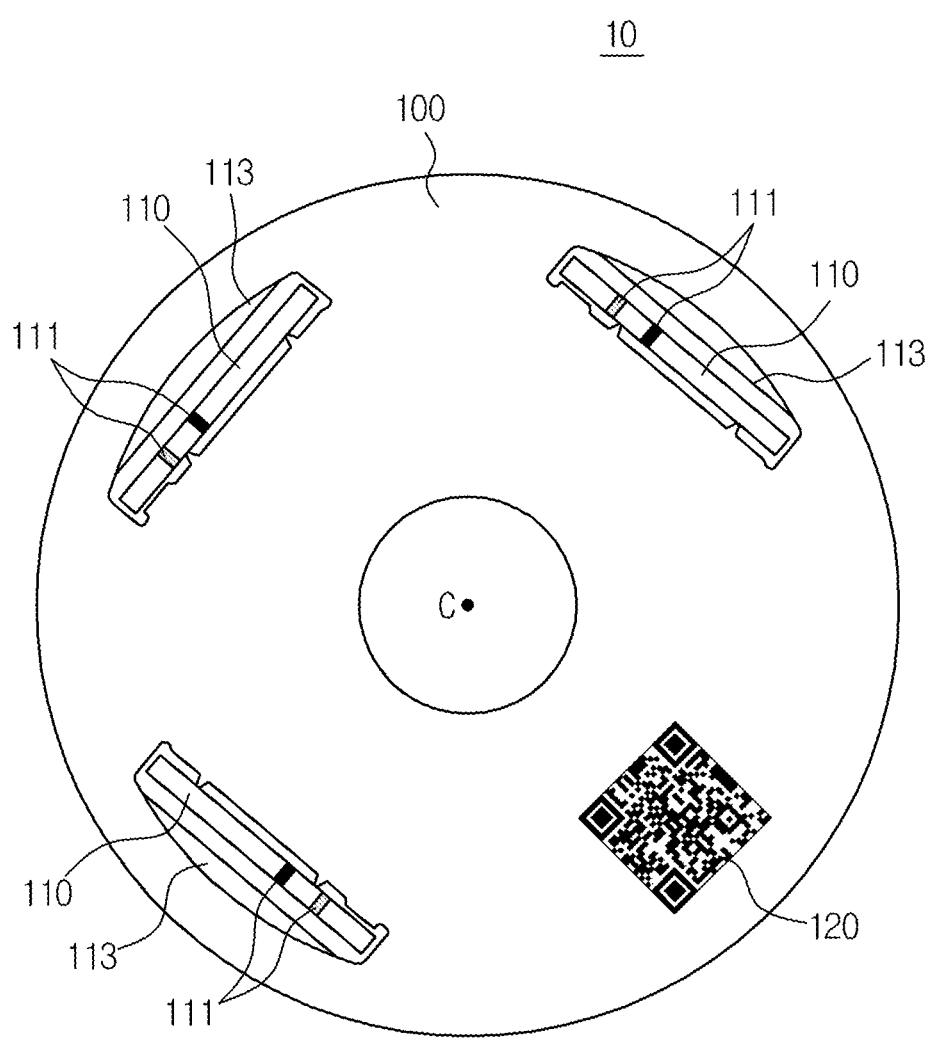
FIG. 2 shows the configuration of the test platform shown in FIG. 1 in detail.

FIG. 1 is a perspective view schematically showing the configuration of a test platform 10 in accordance with an exemplary embodiment, and FIG. 2 is a rear view showing the configuration of the test platform 10 shown in FIG. 1 in detail.

Referring to FIGS. 1 and 2, the test platform 10 includes a body 100, a plurality of reference materials 110 formed on the body 100, and a tag 120.

The body 100 may be made of various materials, such as polymethyl methacrylate (PMMA) as acrylic which can be easily molded and whose surface is biologically inactive, a plastic material (for example, polydimethylsiloxane (PDMS), polycarbonate (PC), polypropylene, polyvinyl alcohol, polyethylene), glass, mica, silica, a silicon wafer, etc. However, the above-mentioned materials are only exemplary, and the body 100 may be made of other materials having chemical, biological stability, optical transparency, and mechinability.

The body 100 may be formed by stacking a plurality of plates. In the contact surfaces of two plates, engraved structures such as chambers may be formed. A general microfluidic device may provide a space for accommodating a fluid therein and a passage for moving the fluid inside the body 100 by bonding two plates. The two plates may be bonded by various methods, such as bonding using an adhesive or a double-sided adhesive tape, ultrasonic welding, laser welding, etc.

In the exemplary embodiment shown in FIGS. 1 and 2, a disc-shaped body is used, however, the body 100 may have a fan shape, etc. that can be held in and rotated on a rotatable frame, instead of a disc shape which is itself rotatable, or the body 100 may have a polygon shape as long as it is rotatable. Hereinafter, the case in which the body 100 is has a disc shape will be described as an example.

As shown in FIGS. 1 and 2, the reference materials 110 and the tag 120 are provided on the body 100.

Figure 5:
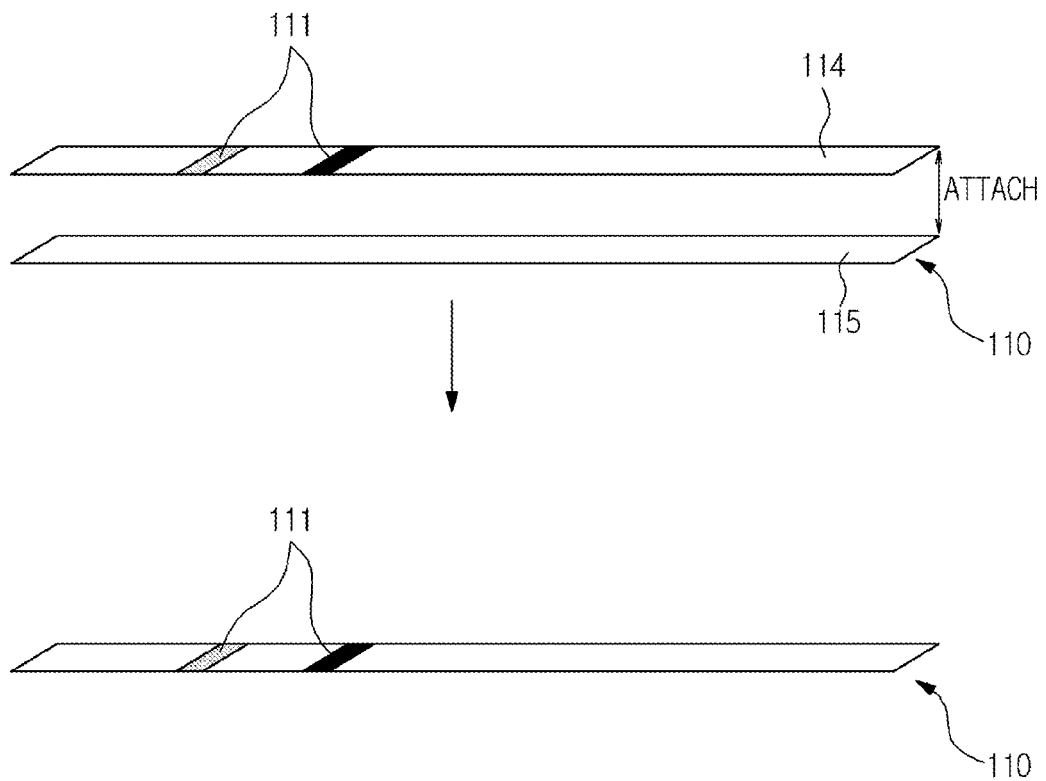
FIG. 5 shows a reference material provided in a test platform in accordance with an exemplary embodiment.

As shown in FIG. 5, each reference material 110 may be formed by attaching a print film 114 on which a plurality of predetermined colors 111 are printed on a reactor 115.

The reactor 115 may be a reactor that is used in a general reactor-type microfluidic device for immunoassay.

The print film 114 which is attached on the reactor 115 may be made by processing various well-known materials having transparency.

However, forming each reference material 110 by attaching the print film 114 on the reactor 115 is only an example, and the reference material 110 on which colors are printed may be formed by other various methods such as using a strip, etc.

Two or more colors 111 may be printed on the print film 114, and the individual colors 111 may be printed with various shapes, various thicknesses, and various brightnesses. The colors 111 may be formed to have different absorbances.

In the exemplary embodiment of FIGS. 1 and 2, two colors 111 are printed, however, this is only exemplary, and three or more colors may be printed.

As such, the reference materials 110 are fabricated by attaching the print film 114 on which the colors 111 are printed on the reactor 115.

Since if serum, etc. are absorbed in a reactor and a reaction occurs in a reactor type microfluidic device, a test apparatus (1000 of FIGS. 6 and 7) photographs the reactor to detect presence/absence of a desired material, the performance of a detection module (1410 of FIGS. 6 and 7) may be tested under an environment similar to an actual detection environment by fabricating the reference materials 110 in such a manner to attach the print film 114 on the reactor 115 that is actually used in the reactor type microfluidic device.

The tag 120 may be a one-dimensional (1D) barcode, a two-dimensional (2D) barcode such as a quick response (QR) code, or a radio frequency identification (RFID) tag. The tag 120 is provided on the rear surface of the test platform 10 in such a manner to be attached on the surface of the test platform 10 without being accommodated in a separate receptor, so that the light receiver 1411 (see FIGS. 6 and 7) of the detection module 1410 can read the tag 120.

The tag 120 includes identification information for informing the test apparatus 1000 that the corresponding platform 10 is a test platform, and also includes a reference value with respect to the results of detection based on light passed through the individual reference materials 110.

Since the test apparatus 1000 should be able to determine, when the test platform 10 is loaded in the test apparatus 1000, whether the corresponding platform 10 is a microfluidic device for immunoassay or a test platform for testing the detection module 1410 in order to properly execute a predetermined algorithm according to the kind of a platform, the tag 120 includes the identification information.

If the test apparatus 1000 reads the tag 120 and determines that the corresponding platform 10 is a test platform, the test apparatus 1000 tests the detection module 1410 according to a predetermined algorithm for a test platform.

The reference value provides criteria for determining whether the results of detection based on light passed through the individual reference materials 110 by the light receiver 1411 of the detection module 1410 are within a range of results indicating that the light receiver 1411 needs to be corrected. The reference value may be a single value, however, the reference value may be a range having upper and lower limits. That is, the reference value may be stored as a reference range having upper and lower limits set for each reference material 110.

For example, if three reference materials 10 are provided, three reference values are stored in the tag 120, the light receiver 1411 of the detection module 1410 detects light passed through each reference material 110, and the test apparatus 1000 compares the result of the detection to the corresponding reference value to determine whether the light receiver 1411 needs to be corrected. If the result of the detection is within a reference range, it is determined that the light receiver 1411 of the detection module 1410 does not need to be corrected since the light receiver 1411 operates normally, and if the result of the detection is out of the reference range, it is determined that the light receiver 1410 needs to be corrected. If it is determined that the light receiver 1411 needs to be corrected, a detection condition of the light receiver 1411 is corrected. Correction of the light receiver 1411 will be described in detail later.

The reference value is a detection value acquired by testing the test platform 10 in the test apparatus 1000, and the reference value is coded and stored in the tag 120.

If the tag 120 is an RFID tag, the detection module 1410 may include an RFID reader.

The tag 120 and the reference materials 110 are positioned at predetermined locations on the test platform 10 in such a manner to be separated from each other along the outer circumferential area of the test platform 10.

The location of each reference material 110 is stored in the tag 120, and the test apparatus 100 reads the tag 120 to recognize the location of each reference material 110.

Since the locations of the individual reference materials 110 can be more easily recognized if the tag 120 and the reference materials 110 are arranged with the same angle (at equal intervals) on the test platform 10, it may be desirable to arrange the tag 120 and the reference materials 110 on the test platform 10 such that the same angle is formed therebetween. The tag 120 and the three reference materials 110 shown in FIGS. 1 and 2 are arranged with the same angle or interval of 90 degrees.

The reference materials 110 may be placed in receptors 113 provided in the form of chambers in the body 100

Figure 3:
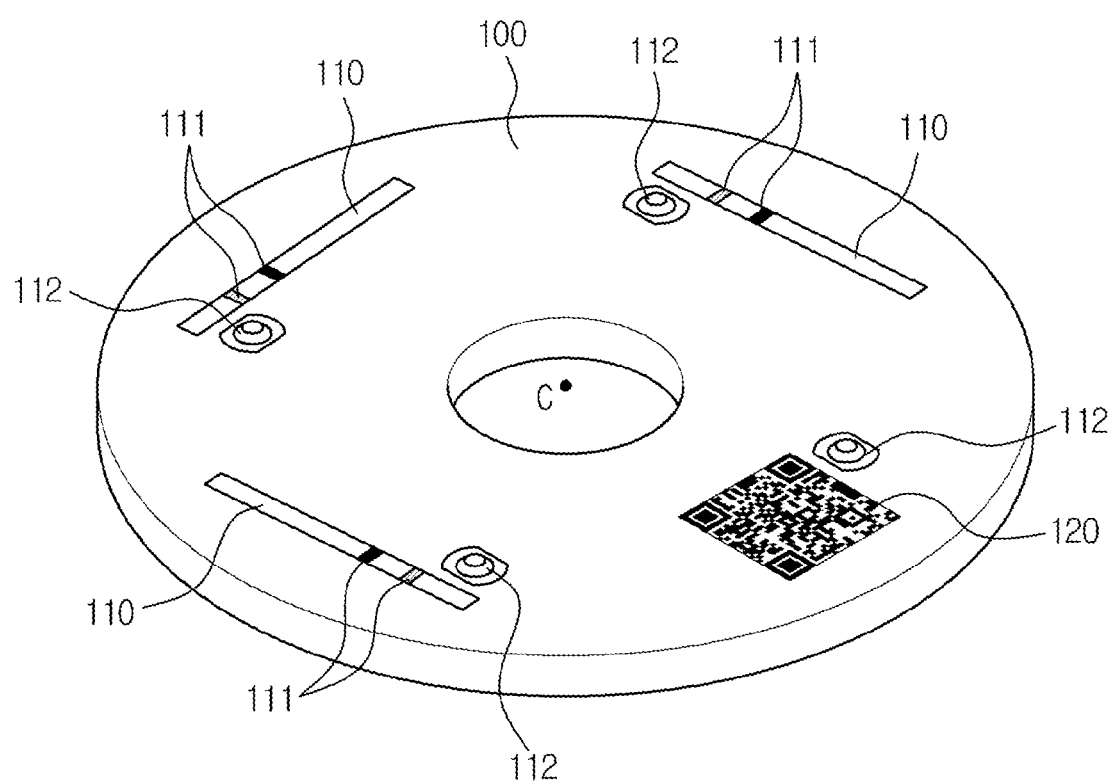
FIG. 3 schematically shows the configuration of a test platform in accordance with another exemplary embodiment.
Figure 4:
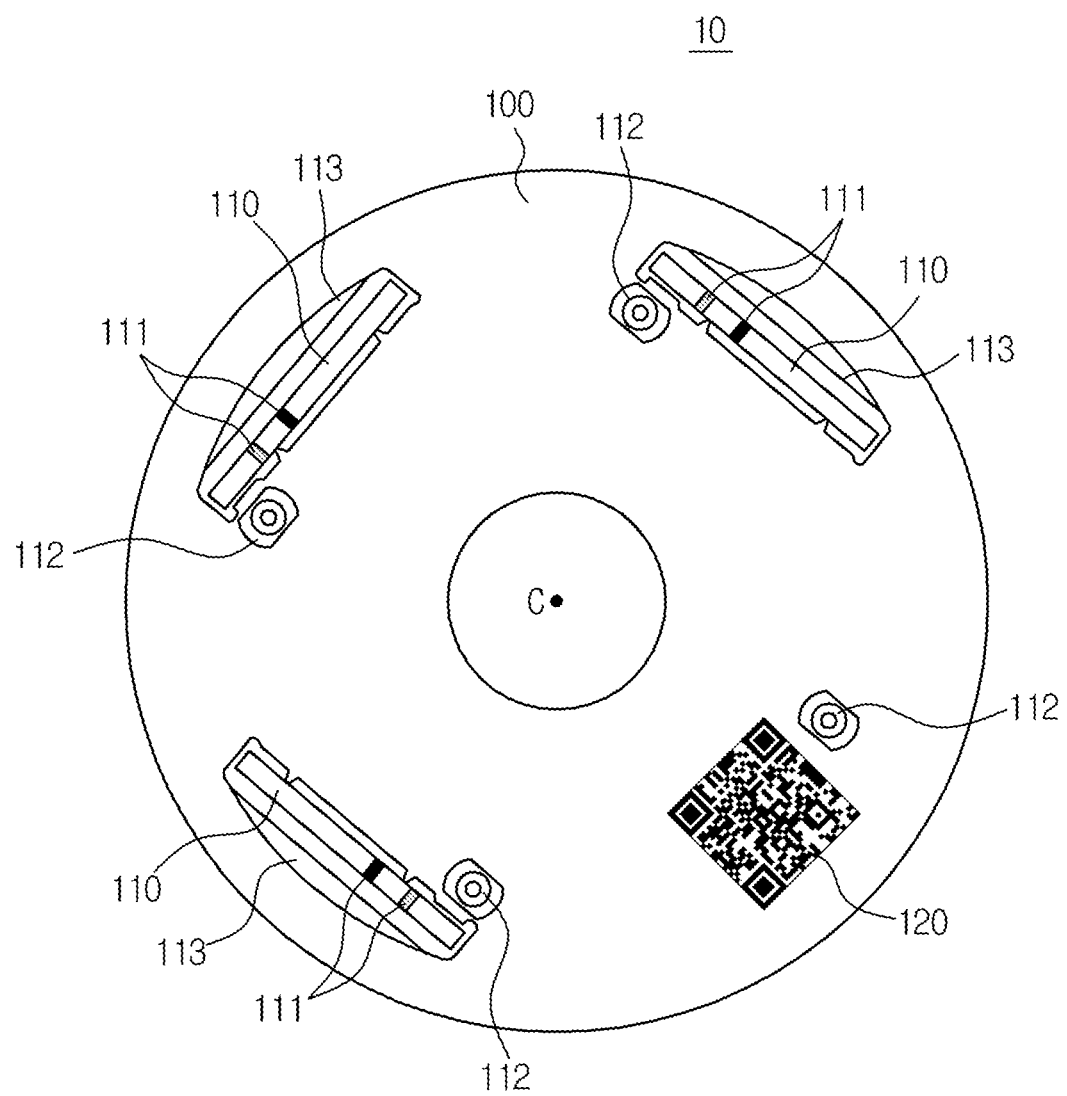
FIG. 4 shows the configuration of the test platform shown in FIG. 3 in detail.

FIG. 3 is a perspective view schematically showing the configuration of a test platform 10 in accordance with another exemplary embodiment, and FIG. 4 is a rear view showing the configuration of the test platform 10 shown in FIG. 3 in detail.

Referring to FIGS. 3 and 4, the test platform 10 includes a body 100, a plurality of reference materials 110 and a tag 120 formed on the body 100, and a plurality of magnetic substances 112 respectively disposed adjacent to the reference materials 110 and the tag 120.

The test platform 10 according to the exemplary embodiment of FIGS. 3 and 4 has the same configuration as the exemplary embodiment of FIGS. 1 and 2 except that the magnetic substances 112 are arranged adjacent to the reference materials 110 and the tag 120. Therefore, descriptions about only the magnetic substances 112 will be given in order to avoid repeated descriptions.

The magnetic substances 112 are provided on the body 100, and accommodating chambers for accommodating the magnetic substances 112 may be formed in the body 100. The accommodating chambers are formed such that the magnetic substances 112 can be exposed on the surface of the test platform 10. Due to the magnetic substances 112, magnets 1413 mounted on a detection module 1410 of a test apparatus 1000 (see FIGS. 13 and 14), which will be described later, can effectively apply an attraction force to the magnetic substances 112.

The magnetic substances 112 are respectively disposed adjacent to the tag 120 and the reference materials 110. As such, by placing the magnetic substances 112 adjacent to the tag 120 and the reference materials 110, the magnets 1413 of the detection module 1410 apply an attraction force to the magnetic substances 112 disposed adjacent to the tag 120 or the reference materials 110 facing the light receiver 1411 when the tag 120 or the reference materials 110 has moved to a location at which they face the light receiver 1411 of the detection module 1410, and the state in which the tag 120 or the reference materials 110 face the light receiver 1411 can be maintained while the light receiver 1411 photographs the tag 120 or the reference materials 110.

Accordingly, the locations of the magnetic substances 112 and the magnets 1413 of the detection module 1410 may be determined such that the light receiver 1411 of the detection module 1410 faces the tag 120 or the reference materials 110 of the test platform 10 when the magnetic substances 112 of the test platform 10 face the magnets 1413 mounted on the detection module 1410 of the test apparatus 1000. This will be readily understood by referring to drawings related to the test apparatus 1000 which will be described later.

The magnetic substances 112 may be ferromagnetic substances, such as iron, cobalt, nickel, etc., having a high magnetization intensity and capable of acting as strong magnets such as permanent magnets, or the magnetic substances 112 may be paramagnetic substances, such as chrome, platinum, manganess, aluminum, etc., capable of acting as magnets when another magnet approaches since their magnetization intensities increase by another magnet although they cannot act as magnets themselves.

The magnetic substances 112 are provided in correspondence to the number of the tag 120 and the reference materials 110 provided on the test platform 10.

Figure 6:
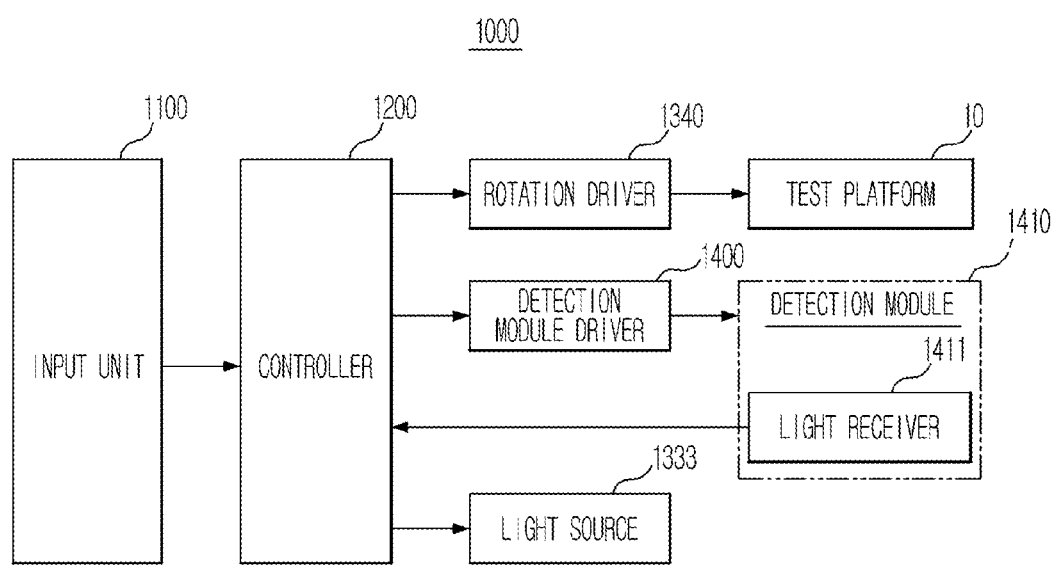
FIG. 6 is a block diagram showing the configuration of a test apparatus in accordance with an exemplary embodiment.
Figure 7:
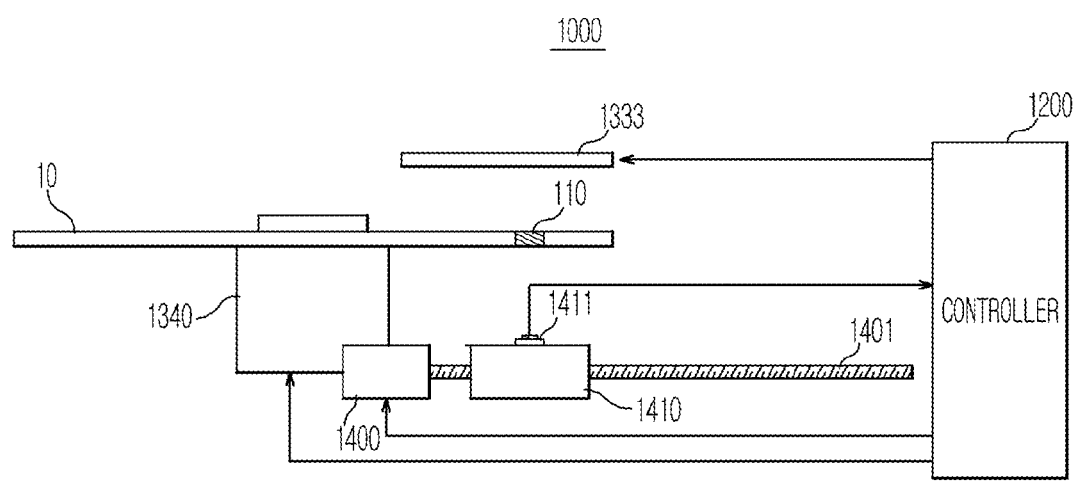
FIG. 7 is a conceptual view showing the configuration of the test apparatus shown in FIG. 6.

FIG. 6 is a block diagram showing the configuration of a test apparatus 1000 in accordance with an exemplary embodiment, and FIG. 7 is a side view conceptually showing the configuration of the test apparatus 1000 shown in FIG. 6.

The test apparatus 1000 includes a rotation driver 1340 for rotating a test platform 10, a light source 1333 for irradiating light to the test platform 10, a detection module 1410 including a light receiver 1411 for reading a tag 120 or detecting reference materials 110 through light irradiated by the light source 1333, a detection module driver 1400 for moving the detection module 1410 in a radial direction, an input unit 1100 for receiving a user's command, and a controller 1200 for controlling operations and functions of the test apparatus 100 according to a command input through the input unit 1100.

Since the test platform 10 has the same configuration as the test platform 10 described above with reference to FIGS. 1 through 5, a detailed description thereof will be omitted.

The rotation driver 1340 may include a spindle motor, and when the test platform 10 is loaded, the rotation driver 1340 rotates the test platform 10 under the control of the controller 1200. The rotation driver 1340 receives signals output from the controller 1200 to repeatedly make rotations and stops, thereby moving the tag 120 or the reference materials 110 of the test platform 10 to a desired location.

Also, the rotation driver 1340 may include a motor driver for controlling the angular position of the test platform 10. For example, the motor driver may include a step motor or a direct-current motor.

The light source 1333 may be implemented as an area light source having a wide emission area and capable of uniformly irradiating light so that light can be irradiated on a predetermined area of the test platform 10. For example, the light source 1333 may be a back light unit.

The light source 1333 may be positioned in the same direction as the light receiver 1411. However, as shown in FIG. 7, the light source 1333 is positioned to face the light receiver 1411. FIG. 7 shows an example in which the light source 1333 and the light receiver 1411 are positioned at the upper location and at the lower location, respectively, with the test platform 10 in between, however, the positions of the light source 1333 and the light receiver 1411 may be reversed. The light source 1333 may adjust an irradiation amount of light under the control of the controller 1200.

The light receiver 1411 receives light that is irradiated by the light source 1333 and passes through the tag 120 or the reference materials 110 to thus read the tag 120 or detect the reference materials 110. The light receiver 1411 may be implemented as a complementary metal-oxide semiconductor (CMOS) image sensor or a charge coupled device (CCD) image sensor.

If the light passed through the tag 120 or the reference materials 110 is received by the light receiver 1411 and thus an image for the tag 120 or the reference materials 110 is acquired, the controller 1200 may acquire information stored in the tag 120 through the image, and detect an amount of light passed through the reference materials 110.

In the test apparatus 1000 according to the current exemplary embodiment, the light receiver 1411 is installed in the detection module 1410 that can move in the radial direction, in order to detect the tag 120 and the plurality of reference materials 110 of the test platform 10 through the single light receiver 1411.

Figure 8:
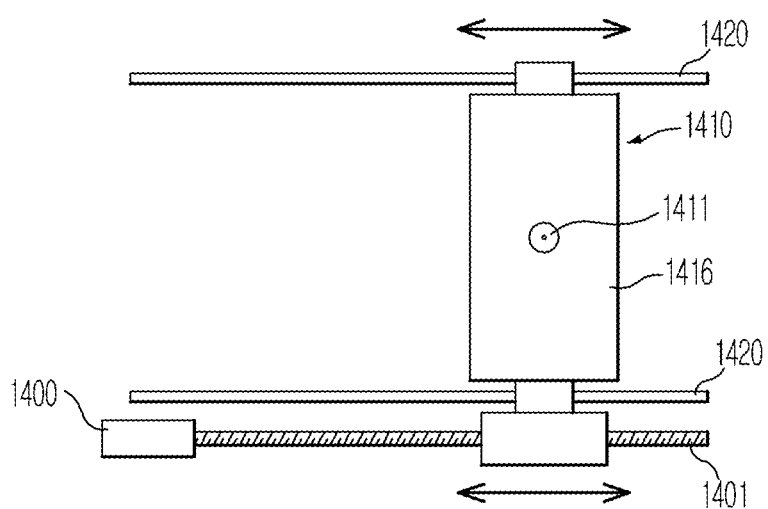
FIGS. 8 and 9 show a detection module moving in a radial direction in the test apparatus illustrated in FIG. 6.
Figure 9:
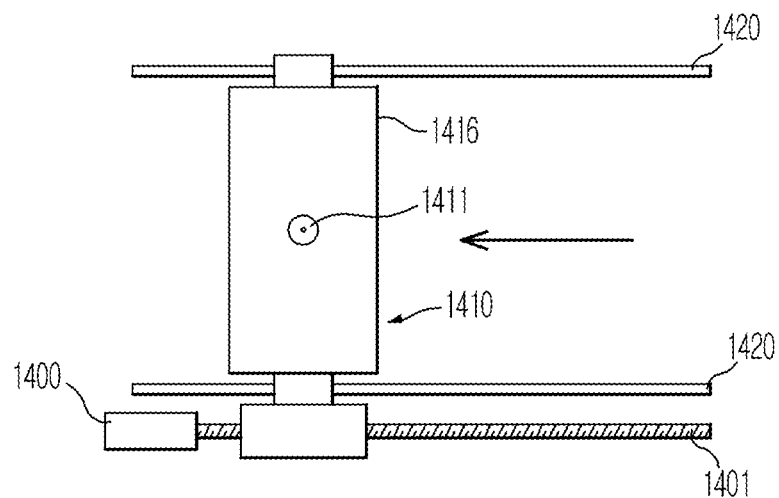

FIGS. 8 and 9 show the detection module 1410 moving in the radial direction, wherein the detection module 1410 is shown from the top.

Referring to FIGS. 8 and 9, the detection module 1410 may move in the radial direction by driving power supplied by the detection module driver 1400. The detection module driver 1400 may be implemented as a feeding motor or a stepping motor.

The movement distance of the detection module 1410 may be longer than the radius of the test platform 10. However, the movement distance of the detection module 1410 may be an arbitrary distance by which the detection module 1410 can move to near the center of the test platform 10 from out of the rim of the test platform 10.

The detection module 1410 may include a plate 1416 on which components such as the light receiver 1411 are mounted. The detection module 1410 may slide in the radial direction along two guide units 1420 for guiding stable radial-directional movement. Each guide unit 1420 may be in the shape of a crossbar. The plate 1416 may be coupled to the guide units 1420 to move along the guide units 1420. The plate 1416 is slidably coupled to the guide units 1420 to enable the detection module 1410 to move along the guide units 1420, while supporting the detection module 1410.

Also, the detection module 1410 is connected to a power transfer unit 1401 so that power generated by the detection module driver 1400 is transferred to the detection module 1410 through the power transfer unit 1401 to move the detection module 1410 in the radial direction. That is, if the detection module driver 1400 is driven so that power is transferred to the detection module 1410 through the power transfer unit 1401, the detection module 1410 moves in the radial direction along the power transfer unit 1401 and the guide units 1420.

FIG. 7 shows an example in which the detection module 1410 is positioned below the test platform 10 and the light source 1333 is positioned above the test platform 10, however, this is only exemplary, and the positions of the detection module 1410 and the light source 1333 may be reversed.

Figure 10:
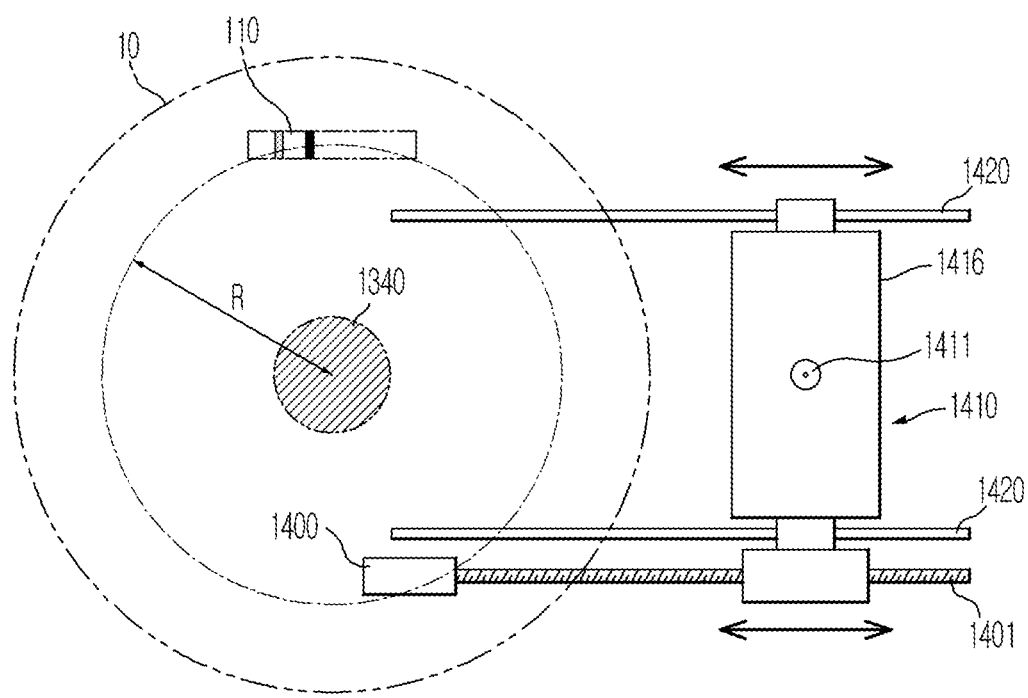
FIGS. 10, 11, and 12 are views for explaining operation in which a reference material moves to face a light receiver of the detection module by movement of the detection module and rotation of a test platform in the test apparatus illustrated in FIG. 6.
Figure 11:
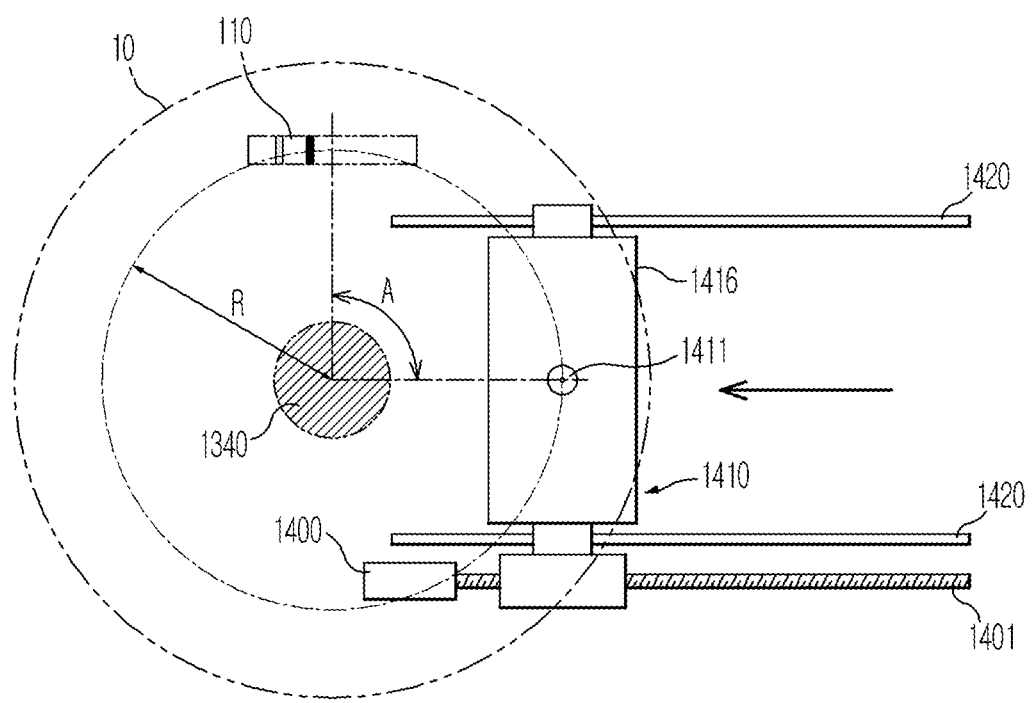
Figure 12:
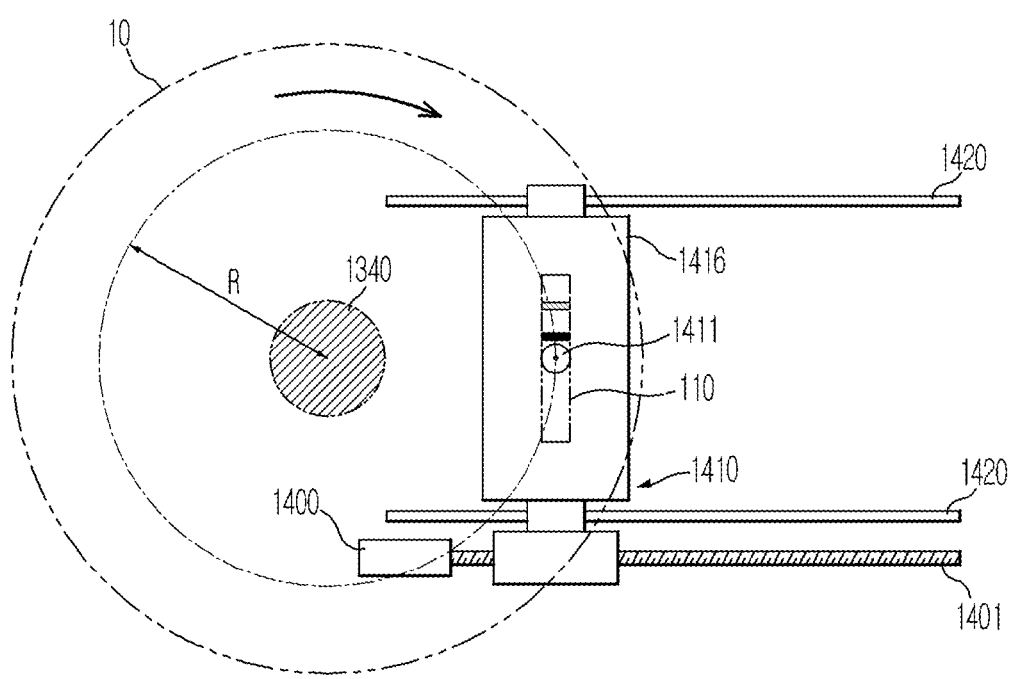

FIGS. 10, 11, and 12 are top views for explaining operation in which the tag 120 and the reference material 110 move to face the light receiver 1411 of the detection module 1410 by movement of the detection module 1410 and rotation of the test platform 10 in the test apparatus 1000 in accordance with the exemplary embodiment. For convenience of description, only one reference material 110 is shown on the test platform 10. Since operation in which the tag 120 moves to face the light receiver 1411 is the same as operation in which the reference material 110 moves to face the light receiver 1411, the following description will be given based on the reference material 110.

In order to clearly show the movement of the detection module 1410, the test platform 10 positioned above the detection module 1410 is denoted by dotted lines, and the detection module 1410 positioned below the test platform 10 is denoted by solid lines.

FIG. 10 shows a state in which the test platform 10 is stopped with the detection module 1410 positioned below the test platform 10 and outside of the test platform 10 in the radial direction. For convenience of description, other components on the test platform 10 except for the reference material 110 are not shown.

The controller 1200 controls the detection module driver 1400 to move the detection module 1410 in the radial direction so that the detection module 1410 can move to a location corresponding to a radial distance R at which the reference material 110 is positioned.

FIG. 11 shows a state in which the detection module 1410 has moved in the radial direction toward the center of the test platform 10 until the light receiver 1411 of the detection module 1410 arrives at the location corresponding to the radial distance R at which the reference material 110 of the test platform 10 is positioned.

Information about radial distances at which the reference materials 110 of the test platform 10 are positioned may be stored in advance in the controller 1200. Alternatively, as described above, information about the locations (that is, radial distances R and angles A) of the individual reference materials 110 may be stored in the tag 120, and the location information about the reference materials 110 may be acquired from the tag 120.

The controller 1200 controls the detection module driver 1400 using the information such that the light receiver 1411 of the detection module 1410 can move to the location corresponding to the radial distance R at which the reference material 110 is positioned.

If the light receiver 1411 of the detection module 1410 arrives at the location corresponding to the radial distance R at which the reference material 110 of the test platform 10 is positioned, the controller 1200 controls the rotation driver 1340 to rotate the test platform 10 until the reference material 110 of the test platform 10 faces the light receiver 1411 of the detection module 1410.

The controller 1200 determines an angle A between the reference material 110 of the test platform 10 and the light receiver 1411 of the detection module 1410, and controls the rotation driver 1340 to rotate the test platform 10 by the determined angle A.

FIG. 12 shows a state in which the test platform 10 has been stopped after the test platform 10 is rotated until the reference material 110 of the test platform 10 arrives at the location at which the reference material 110 faces the light receiver 1411 of the detection module 1410.

If rotation of the test platform 10 is stopped when the reference material 110 of the test platform 10 arrives at the location at which the reference material 110 faces the light receiver 1411 of the detection module 1410, the controller 1200 controls the light source 1333 to irradiate light to the reference material 110, and the light receiver 1411 receives light irradiated from the light source 1333 and passed through the reference material 110, thereby creating an image of the reference material 110.

The controller 1200 analyzes the image of the reference material 110, and determines information including an amount of light passed through the reference material 110.

Figure 13:
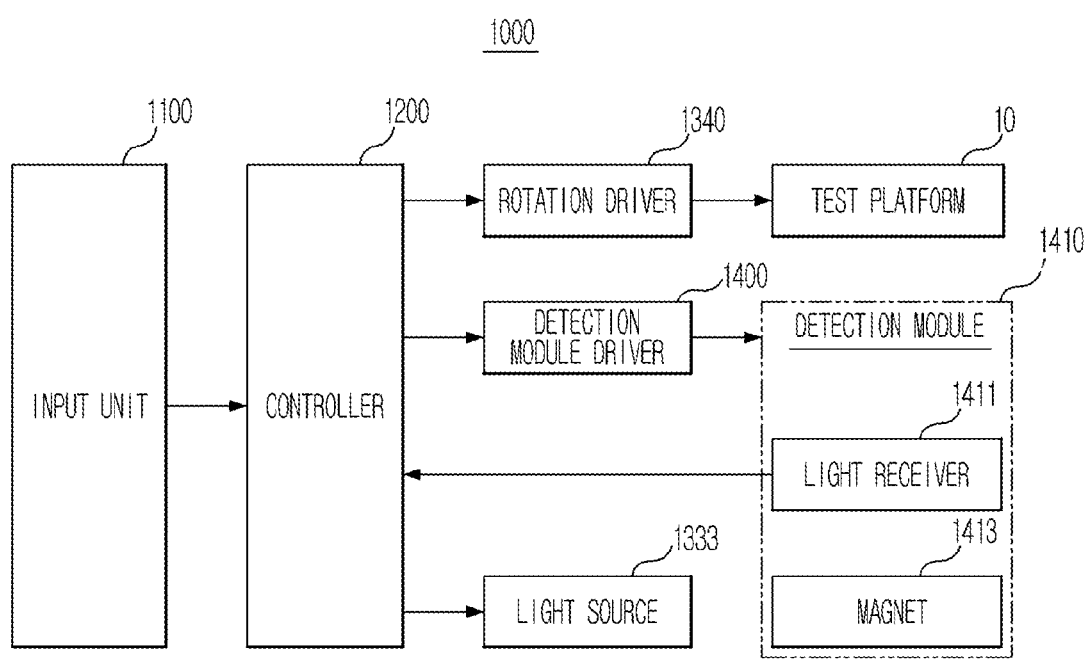
FIG. 13 is a block diagram showing the configuration of a test apparatus in accordance with another exemplary embodiment.
Figure 14:
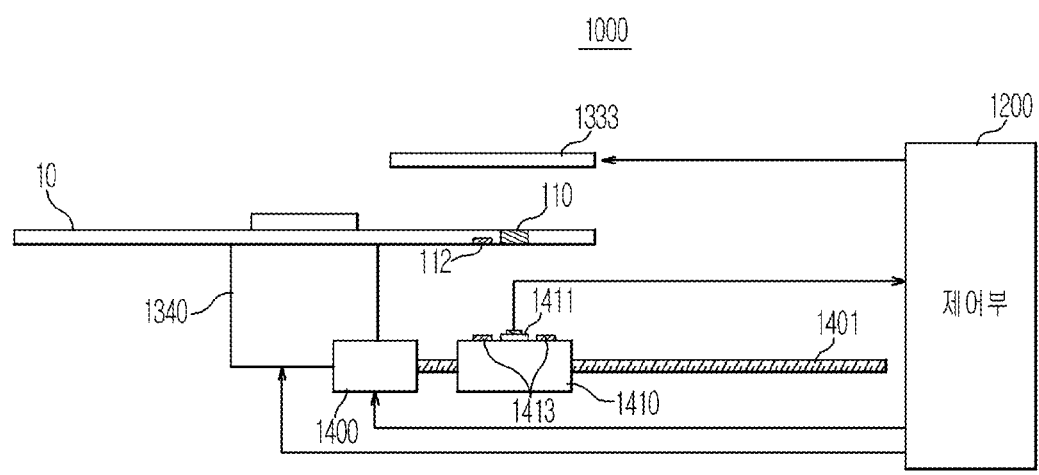
FIG. 14 is a conceptual view showing the configuration of the test apparatus shown in FIG. 13.

FIG. 13 is a block diagram showing the configuration of a test apparatus 1000 in accordance with another exemplary embodiment, and FIG. 14 is a side view conceptually showing the configuration of the test apparatus 1000 shown in FIG. 13.

Referring to FIG. 13, the test apparatus 1000 includes a rotation driver 1340 for rotating a test platform 10, a light source 1333 for irradiating light to the test platform 10, a detection module 1410 including a light receiver 1411 for reading a tag 120 or detecting reference materials 110 through light irradiated by the light source 1333, a detection module 1410 including magnets 1413 for applying an attraction force to magnetic substances 112 mounted on the test platform 10, a detection module driver 1400 for moving the detection module 1410 in the radial direction, an input unit 1100 for receiving a user's command, and a controller 1200 for controlling operations and functions of the test apparatus 100 according to a command input through the input unit 1100.

The current exemplary embodiment is the same as the exemplary embodiment described above with reference to FIGS. 6 through 12 except that the detection module 1410 includes the magnets 1413. Therefore, only the detection module 1410 including the magnets 1413 will be described in detail in order to avoid repeated descriptions.

In the test apparatus 1000 according to the current exemplary embodiment, as shown in FIG. 14, the detection module 1410 may include one or more magnets 1413.

The magnets 1413 mounted on the detection module 1410 applies an attraction force to the magnetic substances 112 formed adjacent to the reference materials 110 or the tag 120 in order to make sure the locations of the reference materials 110 or the tag 120 of the test platform 10. The current exemplary embodiment shows the case in which the magnets 1413 are mounted on the detection module 1410 and the magnetic substances 112 are mounted on the test platform 10, however, it is also possible that the magnetic substances 112 are mounted on the detection module 1410 and the magnet 1413 are mounted on the test platform 10.

If the magnets 1413 of the detection module 1410 face the magnetic substances 112 of the test platform 10, an attraction force is applied from the magnets 1413 to the magnetic substances 112 so that the position of the test platform 10 can be maintained unless another force exceeding the attraction force is applied.

Figure 19:
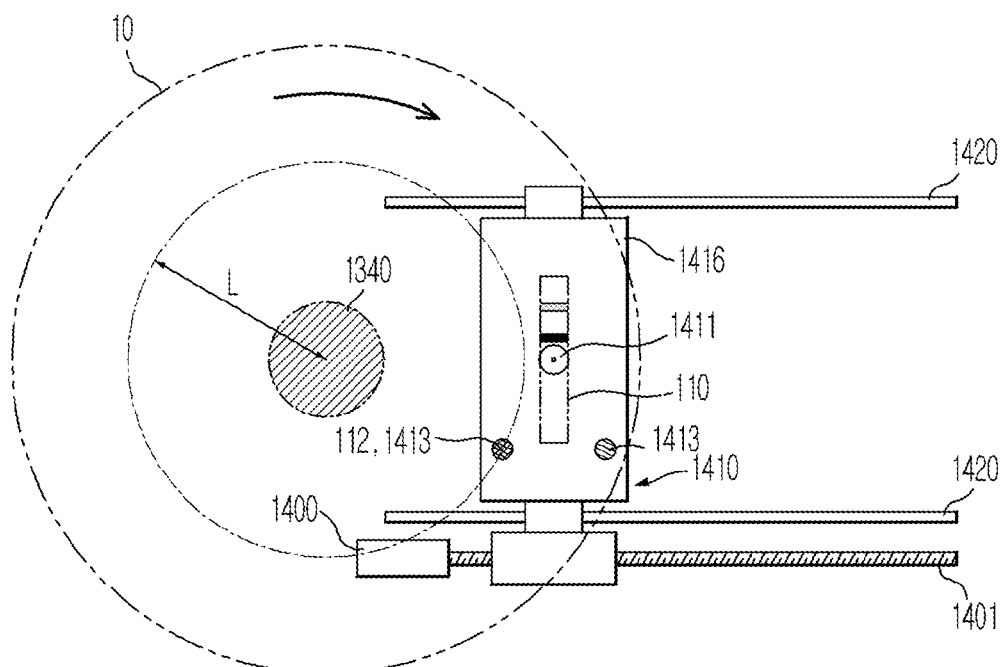

As shown in FIG. 19, the magnets 1413 of the detection module 1410 are positioned such that the reference material 110 faces the light receiver 1411 of the detection module 1410 when the magnetic substances 112 of the test platform 10 face the magnets 1413 and are fixed by an attraction force from the magnets 1413.

That is, when the magnetic substances 112 of the test platform 10 face the magnets 1413 of the detection module 1410, the reference material 10 faces the light receiver 1411.

As such, by mounting the magnets 1413 on the detection module 1410, if the test platform 10 is rotated to move the reference material 110 toward the light receiver 1411 for detecting the reference material 110 until the magnetic substances 112 approach close to the magnets 1413, the magnetic substances 112 are fixed by an attraction force applied by the magnets 1413, so that the test platform 10 is stopped in the state in which the reference material 110 faces the light receiver 1411.

Accordingly, it is possible to stably detect the reference material 110. That is, since the position of the test platform 10 is fixed due to the attraction force between the magnets 1413 and the magnetic substances 112, the reference material 110 can be stably detected even when an external force is applied while the reference material 110 is detected.

FIGS. 14 through 19 show the case in which two magnets 1413 are provided on the detection module 1410. However, the number of the magnets 1413 is not limited. This is because magnetic substances at arbitrary locations on the test platform 10 can be made to face the magnets 1413 of the detection module 1410 through movement in the radial direction of the detection module 1410 and rotation of the test platform 10.

However, since if two or more magnets 1413 are provided on the detection module 1410, the reference material 110 can be made to face the light receiver 1411 through less movement of the detection module 1410 and rotation of the test platform 10 than when one magnet 1413 is provided and another reference material 110 positioned at a different radial distance is detected.

Figure 15:
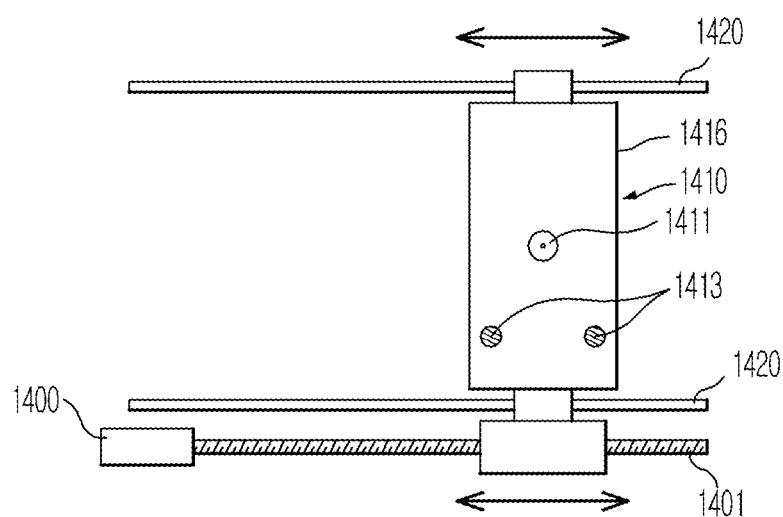
FIGS. 15 and 16 show a detection module moving in a radial direction in the test apparatus illustrated in FIG. 13.
Figure 16:
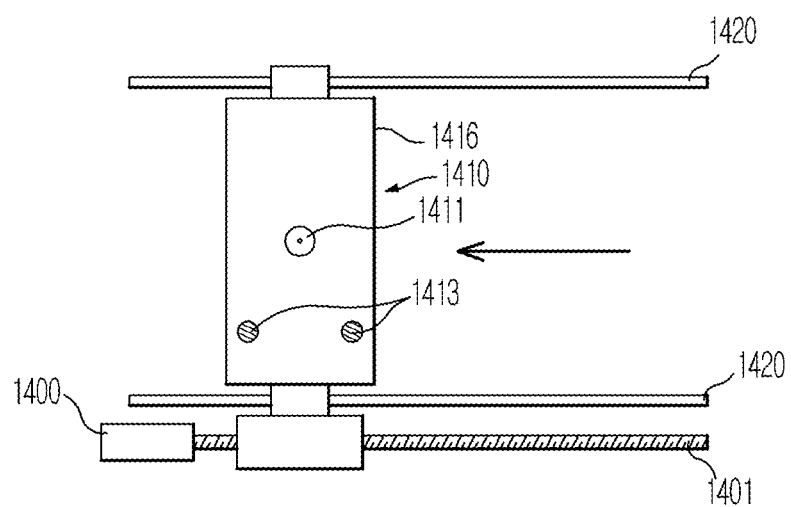

FIGS. 15 and 16 are top views showing the detection module 1410 that moves in the radial direction.

Since the detection module 1410 operates in the same manner as in the exemplary embodiment described above with reference to FIGS. 8 and 9 except that the magnets 1413 are additionally mounted on the detection module 1410, a detailed description thereof will be omitted.

Figure 17:
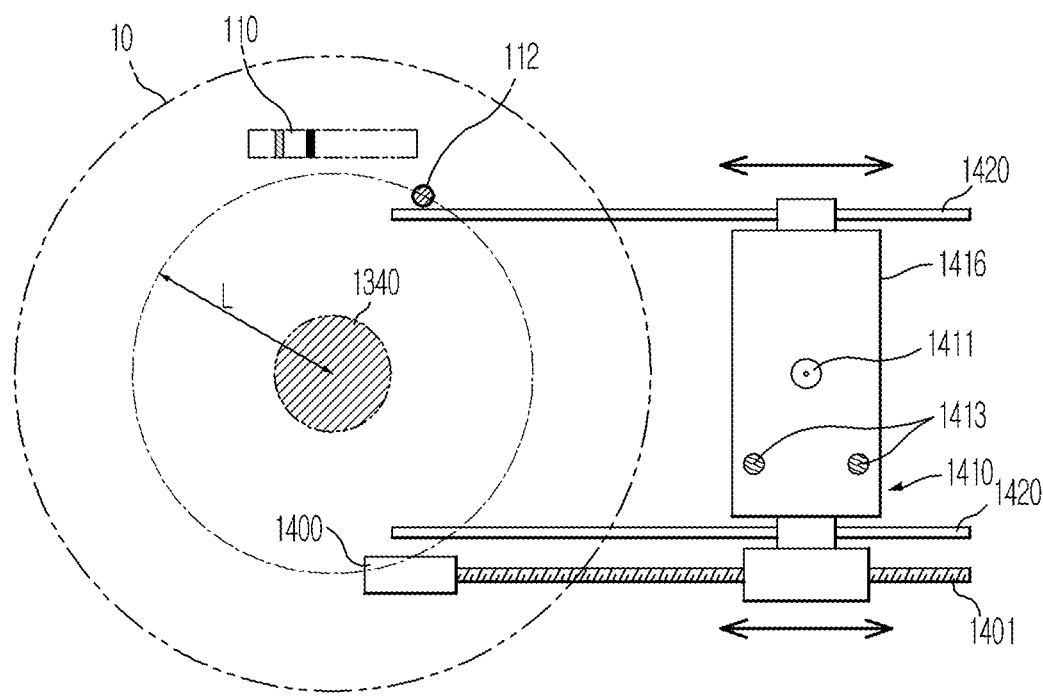
FIGS. 17, 18, and 19 are views for explaining operation in which a reference material moves to face a light receiver of the detection module by movement of the detection module and rotation of a test platform in the test apparatus illustrated in FIG. 13.
Figure 18:
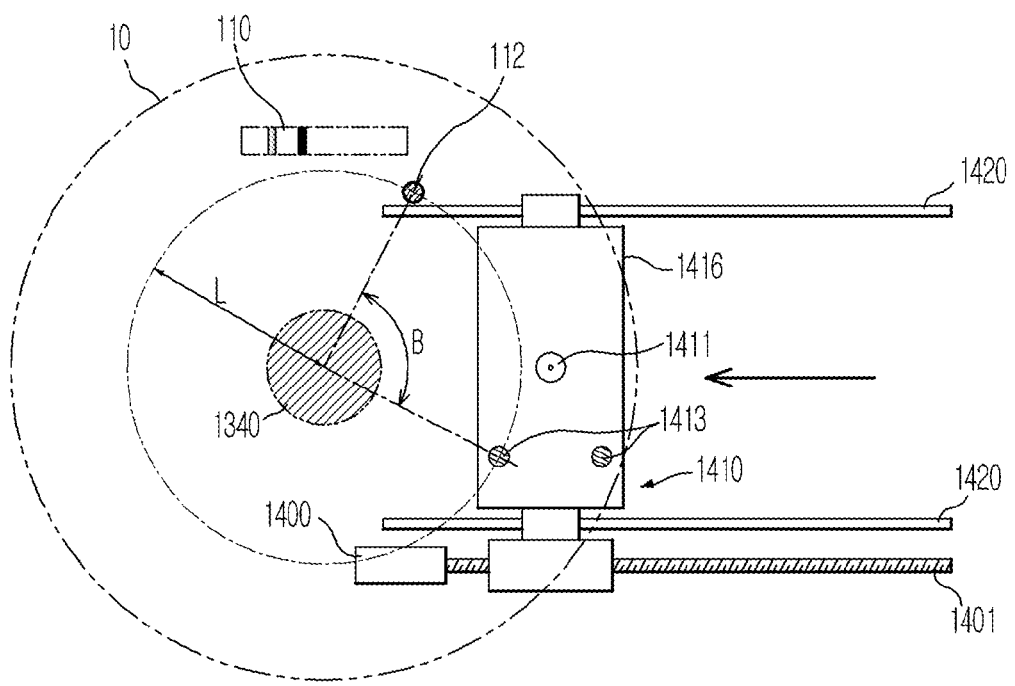

FIGS. 17, 18, and 19 are top views for explaining operation in which the reference material 110 is made to face the light receiver 1411 of the detection module 1410 by movement of the detection module 1410 and rotation of the test platform 10 in the test apparatus 1000 in accordance with the other exemplary embodiment.

In order to clearly show the movement of the detection module 1410, the test platform 10 positioned above the detection module 1410 is denoted by dotted lines, and the detection module 1410 positioned below the test platform 10 is denoted by solid lines.

FIG. 17 shows a state in which the test platform 10 has been stopped, and the detection module 1410 positioned below the test platform 10 and outside of the test platform 10 in the radial direction. For convenience of description, other components on the test platform 10 except for the reference material 110 and the magnetic substance 112 disposed adjacent to the reference material 110 are not shown.

The controller 1200 controls the detection module driver 1400 to move the detection module 1410 in the radial direction so that a magnet 1413 of the detection module 1410 can move to a location corresponding to a radial distance L at which the magnetic substance 112 disposed adjacent to the reference material 110 is positioned.

FIG. 18 shows a state in which the detection module 1410 has moved in the radial direction toward the center of the test platform 10 until the magnet 1413 of the detection module 1410 arrives at the location corresponding to the radial distance L at which the magnetic substance 112 of the test platform 10 is positioned.

Information about radial distances at which the reference materials 110 of the test platform 10 are positioned may be stored in advance in the controller 1200. Alternatively, as described above, information about the locations (that is, radial distances L and angles A) of the magnetic substances 112 disposed adjacent to the individual reference materials 110 may be stored in the tag 120, and the location information about the magnetic substances 112 may be acquired from the tag 120.

The controller 1200 controls the detection module driver 1400 using the information such that the magnet 1413 of the detection module 1410 can move to a location corresponding to a radial distance L at which a magnetic substance 112 disposed adjacent to a target reference material 110 is positioned.

If the magnet 1413 of the detection module 1410 arrives at the location corresponding to the radial distance L at which the magnetic substance 112 of the test platform 10 is positioned, the controller 1200 controls the rotation driver 1340 to rotate the test platform 10 until the magnetic substance 112 of the test platform 10 faces the magnet 1413 of the detection module 1410.

If the magnetic substance 112 approaches close to the magnet 1413 of the detection module 1410, the magnetic substance 112 is fixed at a location at which the magnetic substance 112 faces the magnet 1413 by an attraction force applied to the magnetic substance 112. Thereby, the test platform 10 is stopped in the state in which the reference material 110 of the test platform 10 faces the light receiver 1411 of the detection module 1410.

FIG. 19 shows a state in which the test platform 10 has been fixed by an attraction force applied from the magnet 1413 to the magnetic substance 112 after the test platform 10 is rotated until the magnetic substance 112 of the test platform 10 faces the magnet 1413 of the detection module 1410.

The controller 1200 determines an angle B between the magnetic substance 112 of the test platform 10 and the magnet 1413 of the detection module 1410, and controls the rotation driver 1340 to rotate the test platform 10 by the determined angle B.

If the test platform 10 is stopped after the magnetic substance 112 of the test platform 10 moves to the location at which the reference material 110 faces the magnet 1413 of the detection module 1410, the controller 1200 controls the light source 1333 to irradiate light to the reference material 110, and the light receiver 1411 receives light irradiated from the light source 1333 and passed through the reference material 110, thereby creating an image of the reference material 110.

The controller 1200 analyzes the image of the reference material 110, and determines information including an amount of light passed through the reference material 110.

Figure 20:
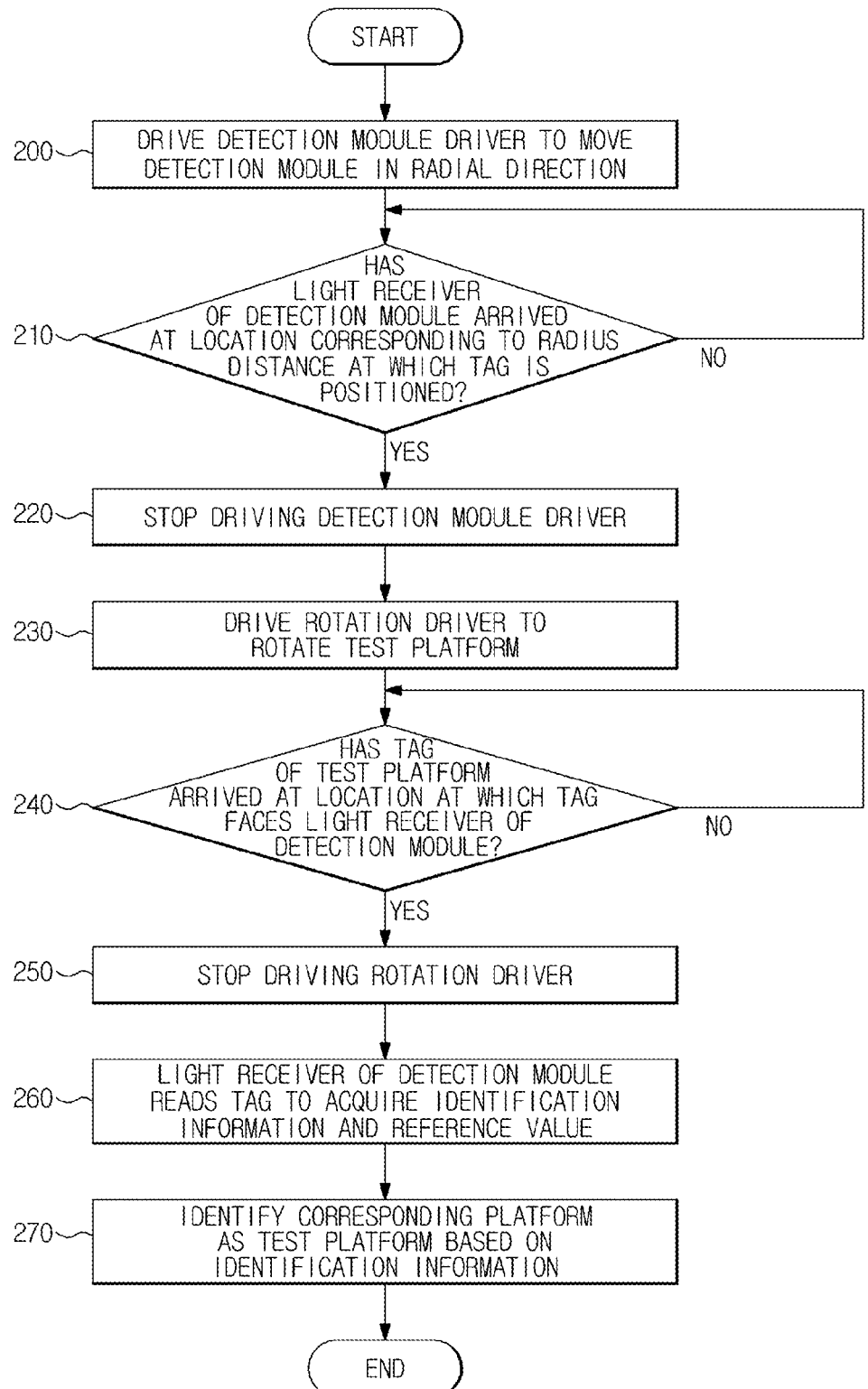
FIGS. 20 and 21 are flowcharts showing a method of controlling the test apparatus illustrated in FIG. 6, in accordance with an exemplary embodiment.
Figure 21:
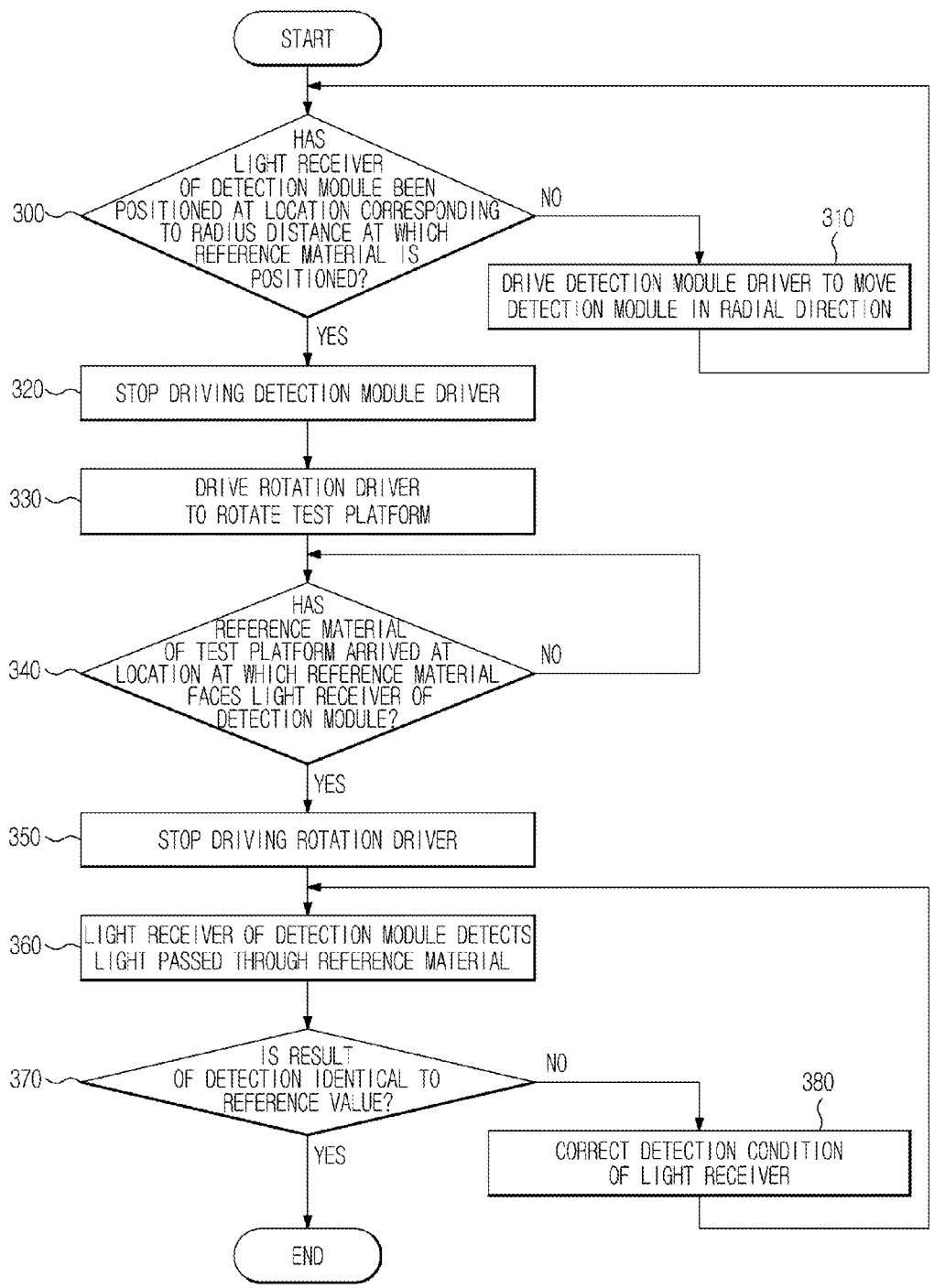

FIGS. 20 and 21 are flowcharts showing a method of controlling the test apparatus 1000 illustrated in FIG. 6, in accordance with an exemplary embodiment, wherein FIG. 20 shows a process of reading the tag 120 (see FIG. 1) to identify the test platform 10, and FIG. 21 show a process of detecting the reference material 110 and correcting the light receiver 1411 of the detection module 1410.

First, referring to FIGS. 6 and 20, if the test platform 10 is loaded in the test apparatus 1000, the controller 1200 drives the detection module driver 1400 to move the detection module 1410 in the radial direction so that the light receiver 1411 of the detection module 1410 moves to a location corresponding to a radial distance at which the tag 120 is positioned (200).

Then, the controller 1200 determines whether the light receiver 1411 of the detection module 1410 has arrived at the location corresponding to the radial distance at which the tag 120 is positioned (210), and if the light receiver 1411 of the detection module 1410 has arrived at the location corresponding to the radial distance at which the tag 120 is positioned, the controller 1200 stops driving the detection module driver 1400 (220).

Information about the radial distance at which the tag 120 is positioned on the test platform 10 may be stored in advance in the controller 1200. The controller 1200 controls the detection module driver 1400 using the information such that the light receiver 1411 of the detection module 1410 can be moved to the location corresponding to the radial distance at which the tag 120 is positioned.

If the light receiver 1411 of the detection module 1410 has arrived at the location corresponding to the radial distance R at which the tag 120 of the test platform 10 is positioned, and the driving of the detection module driver 1400 is stopped, the controller 1200 drives the rotation driver 1340 to rotate the test platform 10 (230).

That is, the controller 1200 controls the rotation driver 1340 to rotate the test platform 10 until the tag 120 of the test platform 10 faces the light receiver 1411 of the detection module 1410.

The controller 1200 calculates an angle A between the tag 120 of the test platform 10 and the light receiver 1411 of the detection module 1410, and controls the rotation driver 1340 to rotate the test platform 10 by the corresponding angle A.

Then, the controller 1200 determines whether the tag 120 of the test platform 10 has arrived at a location at which the tag 120 faces the light receiver 1411 of the detection module 1410 (240), and if the tag 120 has arrived at the location at which the tag 120 faces the light receiver 1411 of the detection module 1410, the controller 120 stops driving the rotation driver 1340 (250).

If the tag 120 arrives at the location at which the tag 120 faces the light receiver 1411 of the detection module 1410, and accordingly the controller 1200 stops driving the rotation driver 1340, the test platform 10 is stopped in the state in which the tag 120 of the test platform 10 faces the light receiver 1411 of the detection module 1410.

If the rotation of the test platform 10 is stopped since the tag 120 of the test platform 10 arrives at the location at which the tag 120 faces the light receiver 1411 of the detection module 1410 and the driving of the rotation driver 1340 is stopped, the controller 1200 drives the light source 1333 such that the light receiver 1411 reads the tag 120 to acquire identification information and a reference value stored in the tag 120 (260). The controller 1200 identifies the corresponding platform 10 as a test platform based on the acquired identification information (270).

The tag 120 includes identification information for informing the test apparatus 1000 that the corresponding platform 10 is a test platform, and a reference value with respect to the results of detection based on light passed through a plurality of reference materials 110.

Since the test apparatus 1000 should be able to determine, when the test platform 10 is loaded in the test apparatus 1000, whether the corresponding platform 10 is a microfluidic device for immunoassay or a test platform for testing the detection module 1410 in order to properly execute a predetermined algorithm according to the kind of a platform, the tag 120 includes the identification information.

If the test apparatus 1000 reads the tag 120 and determines that the corresponding platform 10 is a test platform, the test apparatus 1000 tests the detection module 1410 according to a predetermined algorithm for a test platform.

The reference value provides criteria for determining whether the results of detection based on light passed through the individual reference materials 110 by the light receiver 1411 of the detection module 1410 are within the range of results indicating that the light receiver 1411 needs to be corrected. The reference value may be a single value, however, the reference value may be a range having upper and lower limits. That is, the reference value may be stored as a reference range having upper and lower limits set for each reference material 110. The reference value is a detection value acquired by testing the test platform 10 in the test apparatus 1000, and the reference value is coded and stored in the tag 120.

Referring to FIG. 21, the controller 1200 determines whether the light receiver 1411 of the detection module 1410 is positioned at a location corresponding to a radial distance at which the reference material 110 is positioned (300), and if the light receiver 1411 is not positioned at the location corresponding to the radial distance at which the reference material 110 is positioned, the controller 1200 drives the detection module driver 1400 to move the detection module 1410 in the radial direction until the light receiver 1411 arrives at the location corresponding to the radial distance at which the reference material 110 is positioned (310). If the light receiver 1411 arrives at the location corresponding to the radial distance at which the reference material 110 is positioned, the controller 1200 stops driving the detection module driver 1400 (320).

The process shown in FIG. 21 follows the tag reading process shown in FIG. 20. Since the tag 120 and the reference material 110 may be positioned at locations having the same radial distance, the controller 1200 determines whether the light receiver 1411 is positioned at a location corresponding to a radial distance at which the reference material 110 is positioned, before moving the detection module 1410.

Information about radial distances at which the reference materials 110 are mounted on the test platform 10 may be stored in advance in the controller 1200. Alternatively, as described above, information about the locations (that is, radial distances and angles) of the individual reference materials 110 may be stored in the tag 120, and the location information about the reference materials 110 may be acquired from the tag 120. The controller 1200 controls the detection module driver 1400 using the information such that the light receiver 1411 of the detection module 1410 can move to the location corresponding to the radial distance R at which the reference material 110 is positioned.

If the light receiver 1411 of the detection module 1410 arrives at the location corresponding to the radial distance at which the reference material 110 of the test platform 10 is positioned, and the driving of the detection module driver 1400 is stopped, the controller 1200 drives the rotation driver 1340 to rotate the test platform (330).

That is, the controller 1200 controls the rotation driver 1340 to rotate the test platform 10 until the reference material 110 of the test platform 10 faces the light receiver 1411 of the detection module 1410.

The controller 1200 determines an angle A between the reference material 110 of the test platform 10 and the light receiver 1411 of the detection module 1410, and controls the rotation driver 1340 to rotate the test platform 10 by the corresponding angle A.

Then, the controller 1200 determines whether the reference material 110 of the test platform 10 has arrived at the location at which the reference material 110 faces the light receiver 1411 of the detection module 1410 (340), and if the reference material 110 has arrived at the location at which the reference material 110 faces the light receiver 1411, the controller 1200 stops driving the rotation driver 1340 (350).

If the controller 1200 stops driving the rotation driver 1340 since the reference material 110 has arrived at the location at which the reference material 110 faces the light receiver 1411 of the detection module 1410, the test platform 10 is stopped in the state in which the reference material 110 of the test platform 10 faces the light receiver 1411 of the detection module 1410.

If the rotation of the test platform 10 is stopped since the reference material 110 of the test platform 10 arrives at the location at which the reference material 120 faces the light receiver 1411 of the detection module 1410 and the driving of the rotation driver 1340 is stopped, the light receiver 1411 of the detection module 1410 detects light passed through the reference material 110 (360). That is, if the rotation of the test platform 10 is stopped, the controller 1200 drives the light source 1333 to irradiate light to the reference material 110, and the light receiver 1411 receives light passed through the reference material 110 to detect the reference material 110.

If the light receiver 1411 receives light passed through the reference material 110, the controller 1200 determines whether a result of the detection is identical to the reference value acquired from the tag 120 (370), and if the result of the detection is not identical to the reference value, the controller 1200 corrects a detection condition of the light receiver 1411 (380).

The reference value provides criteria for determining whether the results of detection based on light passed through the individual reference materials 110 by the light receiver 1411 of the detection module 1410 are within the range of results indicating that the light receiver 1411 needs to be corrected. The reference value may be a single value, however, the reference value may be a range having upper and lower limits. That is, the reference value may be stored as a reference range having upper and lower limits set for each reference material 110. The reference value is a detection value acquired by testing the test platform 10 in the test apparatus 1000, and the reference value is coded and stored in the tag 120. The reference value may be an RGB signal value, an YCbCr signal value, or a Gray signal value.

For example, if three reference materials 10 are provided, three corresponding reference values are stored in the tag 120, the light receiver 1411 of the detection module 1410 detects light passed through each reference material 110, and the controller 1200 compares the result of the detection to the corresponding reference value to determine whether the light receiver 1411 needs to be corrected. If the result of the detection is within a reference range, it is determined that the light receiver 1411 of the detection module 1410 does not need to be corrected since the light receiver 1411 operates normally, and if the result of the detection is out of the reference range, it is determined that the light receiver 1410 needs to be corrected. If it is determined that the light receiver 1411 needs to be corrected, a detection condition of the light receiver 1411 is corrected. For example, by correcting conditions or settings of the light receiver 1411, such as shutter speed, the diameter of the aperture, etc., the exposure degree of the light receiver 1411 may be corrected.

After the detection condition of the light receiver 1411 is corrected, the process returns to operation 320 in order to again detect the reference material 110. That is, in order to determine whether the result detected after correction of the detection condition of the light receiver 1411 is identical to the reference value to thus verify whether the correction has been properly conducted, the reference material 110 is again detected.

If the result of the detection is identical to the reference value, it is determined that the correction has been properly conducted, and accordingly, operation of correcting the light receiver 1411 of the detection module 1410 is terminated.

Figure 22:
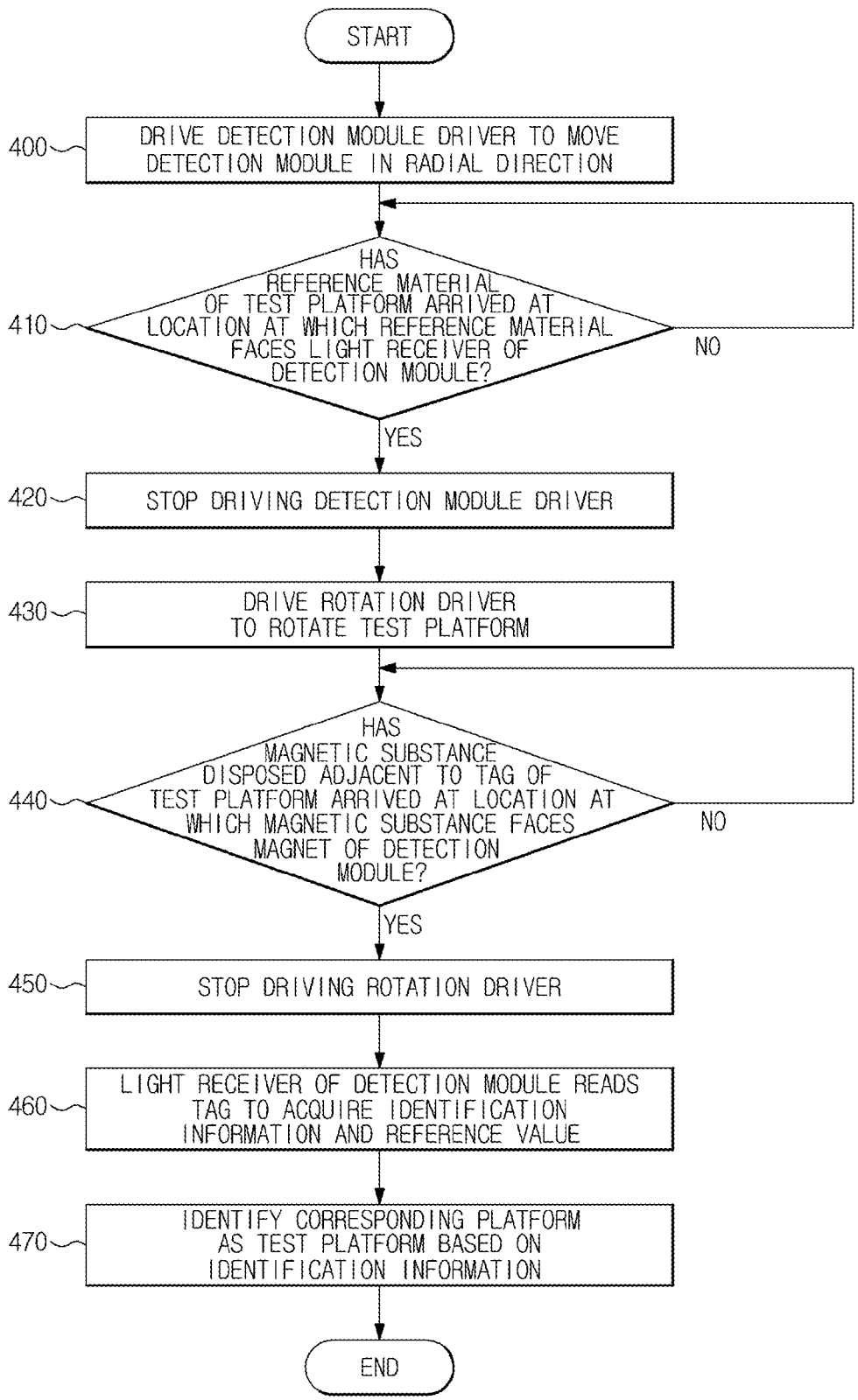
FIGS. 22 and 23 are flowcharts showing a method of controlling the test apparatus illustrated in FIG. 13, in accordance with another exemplary embodiment.
Figure 23:
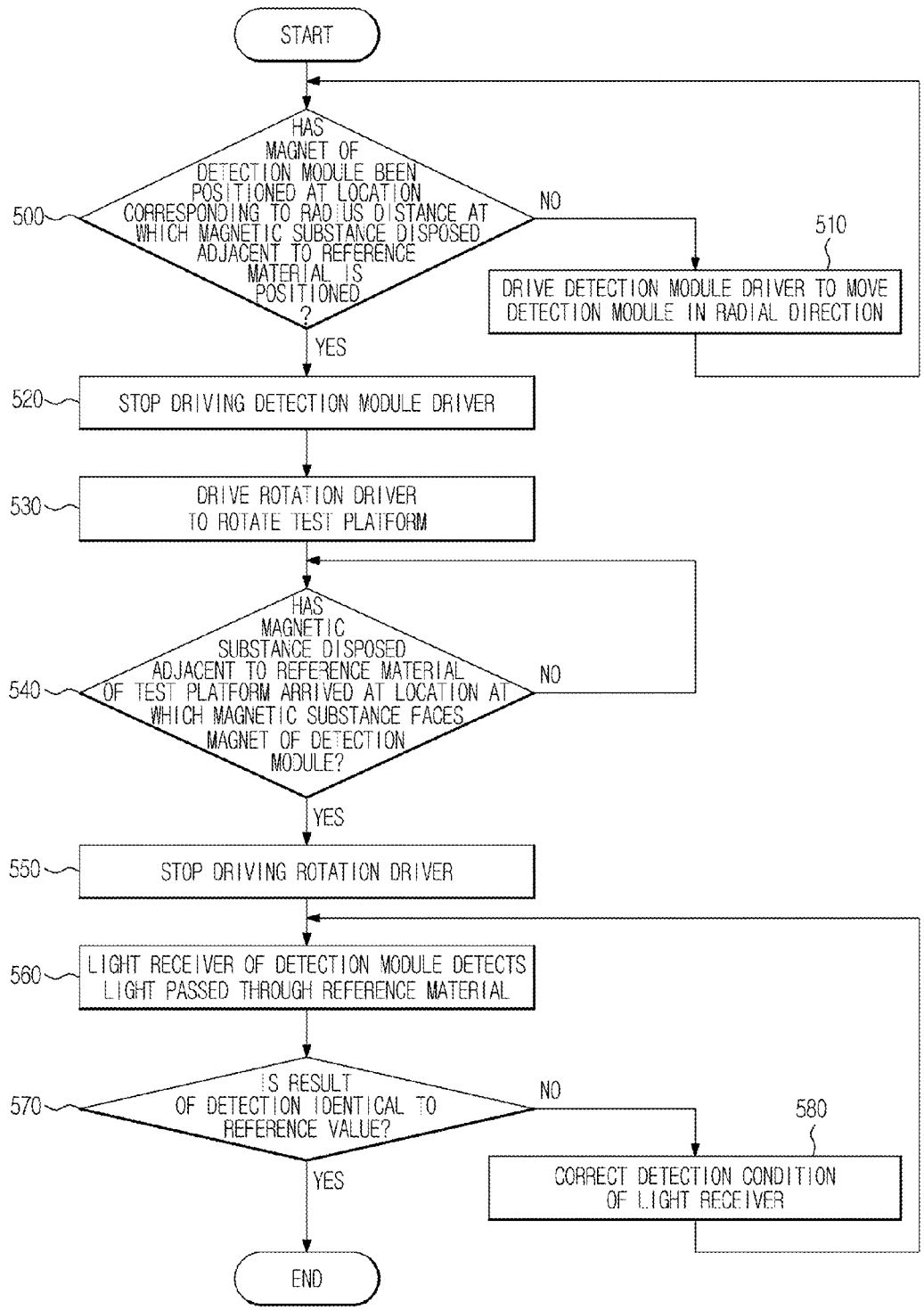

FIGS. 22 and 23 are flowcharts showing a method of controlling the test apparatus 1000 illustrated in FIG. 13, in accordance with another exemplary embodiment, wherein FIG. 22 shows a process of reading the tag 120 (see FIG. 3) to identify the test platform 10, and FIG. 23 shows a process of detecting the reference material 110 to correct the light receiver 1411 of the detection module 1410.

Referring to FIGS. 13 and 22, the controller 1200 drives the detection module driver 1400 to move the detection module 1410 in the radial direction (400).

If the test platform 10 is loaded in the test apparatus 1000, the controller 1200 controls the detection module driver 1400 to move the detection module 1410 in the radial direction such that the magnet 1413 of the detection module 1410 moves to a location corresponding to a radial distance at which the magnetic substance 112 (see FIG. 17) disposed adjacent to the tag 120 (see FIG. 17) is positioned.

The controller 1200 determines whether the magnet 1413 of the detection module 1410 has arrived at the location corresponding to the radial distance at which the magnetic substance 112 disposed adjacent to the tag 120 is positioned (410), and if the magnet 1413 of the detection module 1410 has arrived at the location corresponding to the radial distance at which the magnetic substance 112 disposed adjacent to the tag 120 is positioned, the controller 1200 stops driving the detection module driver 1400 (420).

Information about radial distances at which magnetic substances 112 mounted on the test platform 10 are positioned may be stored in advance in the controller 1200. The controller 1200 controls the detection module driver 1400 using the information such that the magnet 1413 of the detection module 1410 can move to the location corresponding to the radial distance at which the magnetic substance 112 disposed adjacent to the tag 120 is positioned.

If the magnet 1413 of the detection module 1410 has arrived at the location corresponding to the radial distance at which the magnetic substance 112 of the test platform 10 is positioned, and the driving of the detection module driver 1400 is stopped, the controller 1200 drives the rotation driver 1340 to rotate the test platform (430).

That is, the controller 1200 controls the rotation driver 1340 to rotate the test platform 10 until the magnetic substance 112 of the test platform 10 faces the magnet 1413 of the detection module 1410.

The controller 1200 determines an angle between the magnetic substance 112 of the test platform 10 and the magnet 1413 of the detection module 1410, and controls the rotation driver 1340 to rotate the test platform 10 by the corresponding angle.

The controller 1200 determines whether the magnetic substance 112 of the test platform 10 has arrived at the location at which the magnetic substance 112 faces the magnet 1413 of the detection module 1410 (440), and if the magnetic substance 112 has arrived at the location at which the magnetic substance 112 faces the magnet 1413 of the detection module 1410, the controller 1200 stops driving the rotation driver 1340 (450).

If the controller 1200 stops driving the rotation driver 1340 since the reference material 110 has arrived at the location at which the magnetic substance 112 faces the magnet 1413 of the detection module 1410, the magnetic substance 112 is fixed at the location at which the magnetic substance 112 faces the magnet 1413 of the detection module 1410, by an attraction force applied from the magnet 1413 to the magnetic substance 112. Thereby, the test platform 10 is stopped in the state in which the tag 120 of the test platform 10 faces the light receiver 1411 of the detection module 1410.

If the rotation of the test platform 10 is stopped since the magnetic substance 112 of the test platform 10 has arrived at the location at which the magnetic substance 112 faces the magnet 1413 of the detection module 1410 and the driving of the rotation driver 1340 is stopped, the controller 1200 drives the light source 1333 such that the light receiver 1411 reads the tag 120 to acquire identification information and a reference value stored in the tag 120 (460). The controller 1200 identifies the corresponding platform 10 as a test platform based on the acquired identification information (470).

The tag 120 includes identification information for informing the test apparatus 1000 that the corresponding platform 10 is a test platform, and also includes a reference value with respect to the results of detection based on light passed through a plurality of reference materials 110.

Since the test apparatus 1000 should be able to determine, when the test platform 10 is loaded in the test apparatus 1000, whether the corresponding platform 10 is a microfluidic device for immunoassay or a test platform for testing the detection module 1410 in order to properly execute a predetermined algorithm according to the kind of a platform, the tag 120 includes the identification information.

If the test apparatus 1000 reads the tag 120 and determines that the corresponding platform 10 is a test platform, the test apparatus 1000 tests the detection module 1410 according to a predetermined algorithm for a test platform.

The reference value provides criteria for determining whether the results of detection based on light passed through the individual reference materials 110 by the light receiver 1411 of the detection module 1410 are within the range of results indicating that the light receiver 1411 needs to be corrected. The reference value may be a single value, however, the reference value may be a range having upper and lower limits. That is, the reference value may be stored as a reference range having upper and lower limits set for each reference material 110. The reference value is a detection value acquired by testing the test platform 10 in the test apparatus 1000, and the reference value is coded and stored in the tag 120.

Referring to FIG. 23, the controller 1200 determines whether the magnet 1413 of the detection module 1410 is positioned at a location corresponding to a radial distance at which the magnetic substance 112 disposed adjacent to the reference material 110 is positioned (500). If the magnet 1413 is not positioned at the location corresponding to the radial distance at which the magnetic substance 112 is positioned, the controller 1200 drives the detection module driver 1400 to move the detection module 1410 in the radial direction until the magnet 1413 arrives at the location corresponding to the radial distance at which the magnetic substance 112 is positioned (510), and if the magnet 1413 is positioned at the location corresponding to the radial distance at which the reference material 110 is positioned, the controller 1200 stops driving the detection module driver 1400 (520).

The process shown in FIG. 23 follows the tag reading process shown in FIG. 22. Since the magnetic substance 112 disposed adjacent to the tag 120 and the magnetic substance 112 disposed adjacent to the reference material 110 may be positioned at locations corresponding to the same radial distance, the controller 1200 determines whether the magnet 1413 is positioned at a location corresponding to a radial distance at which the magnetic substance 112 disposed adjacent to the reference material 110 is positioned, before moving the detection module 1410.

Information about radial distances at which magnetic substances 112 disposed adjacent to reference materials 110 are positioned may be stored in advance in the controller 1200. Or, as described above, information about the locations (that is, radial distances and angles) of the individual magnetic substances 112 may be stored in the tag 120, and the location information about the magnetic substances 112 may be acquired from the tag 120. The controller 1200 controls the detection module driver 1400 using the information such that the magnet 1413 of the detection module 1410 can move to the location corresponding to the radial distance at which the magnetic substance 112 disposed adjacent to the reference material 110 is positioned.

If the magnet 1413 of the detection module 1410 is positioned at the location corresponding to the radial distance at which the magnetic substance 112 is positioned, and the driving of the detection module driver 1400 is stopped, the controller 1200 drives the rotation driver 1340 to rotate the test platform (530).

That is, the controller 1200 controls the rotation driver 1340 to rotate the test platform 10 until the magnetic substance 112 disposed adjacent to the reference material 110 faces the magnet 1413 of the detection module 1410.

The controller 1200 determines an angle between the magnetic substance 112 of the test platform 10 and the magnet 1413 of the detection module 1410, and controls the rotation driver 1340 to rotate the test platform 10 by the corresponding angle A.

Then, the controller 1200 determines whether the magnetic substance 112 of the test platform 10 has arrived at the location at which the magnetic substance 112 faces the magnet 1413 of the detection module 1410 (540), and if the magnetic substance 112 has arrived at the location at which the magnetic substance 112 faces the magnet 1413 of the detection module 1410, the controller 1200 stops driving the rotation driver 1340 (550).

If the magnetic substance 112 disposed adjacent to the reference material 110 has arrived at the location at which the magnetic substance 112 faces the magnet 1413 of the detection module 1410, and the controller 1200 stops driving the rotation driver 1340, the magnetic substance 112 is fixed at the location at which the magnetic substance 112 faces the magnet 1413, by an attraction force applied from the magnet 1413 to the magnetic substance 112. Thereby, the test platform 10 is stopped in the state in which the reference material 110 of the test platform 10 faces the light receiver 1411 of the detection module 1410.

If the rotation of the test platform 10 is stopped since the magnetic substance 112 of the test platform 10 has arrived at the location at which the magnetic substance 112 faces the magnet 1413 of the detection module 1410 and the driving of the rotation driver 1340 has been stopped, the light receiver 1411 of the detection module 1410 detects light passed through the reference material 110 (560).

That is, if the rotation of the test platform 10 is stopped, the controller 1200 drives the light source 1333 to irradiate light to the reference material 110, and the light receiver 1411 receives light passed through the reference material 110 to detect the reference material 110.

If the light receiver 1411 receives light passed through the reference material 110, the controller 1200 determines whether the result of the detection is identical to the reference value acquired from the tag 120 (570), and if the result of the detection is not identical to the reference value, the controller 1200 corrects a detection condition of the light receiver 1411 (580).

The reference value provides criteria for determining whether the results of detection based on light passed through the individual reference materials 110 by the light receiver 1411 of the detection module 1410 are within the range of results indicating that the light receiver 1411 needs to be corrected. The reference value may be a single value, however, the reference value may be a range having upper and lower limits. That is, the reference value may be stored as a reference range having upper and lower limits set for each reference material 110. The reference value is a detection value acquired by testing the test platform 10 in the test apparatus 1000, and the reference value is coded and stored in the tag 120. The reference value may be an RGB signal value, an YCbCr signal value, or a Gray signal value.

For example, if three reference materials 10 are provided, three reference values are stored in the tag 120, the light receiver 1411 of the detection module 1410 detects light passed through each reference material 110, and the controller 1200 compares the result of the detection to the corresponding reference value to determine whether the light receiver 1411 needs to be corrected. If the result of the detection is within a reference range, it is determined that the light receiver 1411 of the detection module 1410 does not need to be corrected since the light receiver 1411 operates normally, and if the result of the detection is out of the reference range, it is determined that the light receiver 1410 needs to be corrected.

If it is determined that the light receiver 1411 needs to be corrected, a detection condition of the light receiver 1411 is corrected. For example, by correcting conditions of the light receiver 1411, such as shutter speed, the diameter of the aperture, etc., the exposure degree of the light receiver 1411 may be corrected.

After the detection condition of the light receiver 1411 is corrected, the process returns to operation 560 in order to again detect the reference material 110. That is, in order to determine whether the result detected after correction of the detection condition of the light receiver 1411 is identical to the reference value to thus verify whether the correction has been properly conducted, the reference material 110 is again detected.

If the result of the detection is identical to the reference value, it is determined that the correction has been properly conducted, and accordingly, operation of correcting the light receiver 1411 of the detection module 1410 is terminated.

According to the exemplary embodiments, the performance of the detection module of the test apparatus may be easily managed at low cost by using the test platform.

Also, it is possible to reduce a time required for managing the performance of the detection module of the test apparatus.

In addition, through the performance management of the detection module, the results of detection with high accuracy and reliability may be obtained.

Although a few exemplary embodiments have been shown and described, it would be appreciated by those skilled in the art that changes may be made in these embodiments without departing from the principles and spirit of the inventive concept, the scope of which is defined in the claims and their equivalents.

What is claimed is:

1. A test platform comprising:
   a body;
   at least one reference material which is formed on the body and on which at least one color is printed; and
   a tag that stores information related to the test platform determining whether a detection module of a test apparatus comprising at least one hardware processor needs to be corrected,
   wherein the tag includes a reference value with respect to a result of detection regarding the reference material by the detection module, and identification information identifying whether the test platform is a microfluidic device or a test platform testing the detection module of a test apparatus.

2. The test platform according to claim 1, wherein a plurality of colors are printed on the at least one reference material, and the colors are different from each other in at least one of printed shape, brightness, and thickness.

3. The test platform according to claim 1, wherein the tag is formed on the body, and includes a barcode, a quick response (QR) code, or a radio frequency identification (RFID) tag.

4. The test platform according to claim 1, wherein the reference value includes a reference range for each reference material.

5. The test platform according to claim 1, further comprising an accommodator which accommodates the at least one reference material therein.

6. The test platform according to claim 1, further comprising a plurality of magnetic substances disposed adjacent to the at least one reference material and the tag.

7. The test platform according to claim 1, wherein the reference material is a print film on which one or more colors are printed on a reactor.

8. The test platform according to claim 1, wherein the body has a disc shape.

9. A test apparatus comprising at least one hardware processor which implements:
   a light source configured to irradiate light to a platform including a tag;
   a detection module configured to read information stored in the tag of the platform, the detection module including a light receiver configured to face the light source and to receive the light irradiated by the light source; and
   a controller configured to, in response to determining that the platform is identified as a microfluidic device based on identification information included in information read from the tag, control the light source and the light receiver to detect a biochemical reaction occurring in a detection target included in the microfluidic device,
   wherein the controller is configured to, in response to determining that the platform is identified as a test platform based on the identification information, compare a reference value included in the information read from the tag and a result of a detection of a reference material provided on the test platform by the detection module, and to determine whether the detection module needs to be corrected based on a result of the comparison.

10. The test apparatus according to claim 9, wherein the at least one hardware processor further implements:
    a rotation driver configured to rotate the test platform; and
    a detection module driver configured to move the detection module in a radial direction with respect to the test platform,
    wherein the controller controls the detection module driver to move the detection module in the radial direction until the light receiver of the detection module is positioned at a location corresponding to a radial distance at which the tag or the reference material is positioned, and controls the rotation driver to rotate the test platform until the tag or the reference material faces the light receiver.

11. The test apparatus according to claim 9, wherein the light source is an area light source including a backlight unit.

12. The test apparatus according to claim 9, wherein the light receiver includes a charge coupled device (CCD) image sensor or a complementary metal-oxide semiconductor (CMOS) image sensor.

13. The test apparatus according to claim 9, wherein the test platform includes a plurality of magnetic substances disposed adjacent to the tag and the reference material, and
    the detection module includes a plurality of magnets for applying an attraction force to the magnetic substances so that the tag and the reference material are stopped at locations at which the tag and the reference material face the light receiver.

14. The test apparatus according to claim 13, wherein the controller controls the detection module driver to move the detection module in a radial direction until the magnets of the detection module are positioned at locations corresponding to radial distances at which the magnetic substances of the test platform are positioned, and controls the rotation driver to rotate the test platform until the magnetic substances of the test platform face the magnets of the detection module.

15. The test apparatus according to claim 9,
    wherein the controller receives, in response to determining that the light receiver of the detection module detects light passed through one or more colors printed on the reference material, the result of the detection, and compares the result of the detection to the reference value, and
    wherein the controller corrects the light receiver of the detection module in response to determining that the result of the detection is not identical to the reference value.

16. The test apparatus according to claim 9, wherein the reference value includes a reference range set in advance for the reference material.

17. The test apparatus according to claim 9, wherein if the result of the detection is not identical to the reference value, the controller corrects a detection condition of the light receiver such that the result of the detection by the light receiver is identical to the reference value, and
    after the detection condition of the light receiver is corrected, the controller controls the light receiver to detect light passed through one or more colors printed on the reference material, and determines whether the result of the detection is identical to the reference value.

18. A method of controlling a test apparatus comprising at least one hardware processor, the method comprising:
    receiving information stored in a tag of a platform;
    detecting, in response to determining that the platform is identified as a microfluidic device based on identification information included in the received information read from the tag, a biochemical reaction occurring in a detection target included in the microfluidic device;
    comparing, in response to determining that the platform is identified as a test platform based on the identification information included in the received information read from the tag, the reference value included in the received information with a result of a detection of light passed through a reference material provided on the test platform by the detection module; and correcting a light receiver of the detection module if the result of the detection is not identical to the reference value.

19. The method according to claim 18, wherein the receiving the information including the reference value comprises:

moving the detection module in a radial direction with respect to the test platform until the light receiver of the detection module is positioned at a location corresponding to a radial distance at which the tag is positioned on the test platform;

rotating the test platform until the tag faces the light receiver;

receiving the reference value and identification information for identifying the test platform from the light receiver, wherein the light receiver acquires the identification information and the reference value by reading the tag;

storing the identification information and the reference value; and identifying that the test platform is a test platform for testing the detection module based on the identification information.

20. The method according to claim 19, wherein the test platform includes a magnetic substance disposed adjacent to the tag, the detection module includes a magnet applying an attraction force to the magnetic substance so that the tag is stopped at a location at which the tag faces the light receiver, and the moving the detection module in the radial direction comprises moving the detection module in the radial direction until the magnet of the detection module arrives at a location corresponding to a radial distance at which the magnetic substance disposed adjacent to the tag of the test platform is positioned.

21. The method according to claim 20, wherein the rotating the test platform comprises rotating the test platform so that the magnetic substance of the test platform faces the magnet of the detection module when the magnet of the detection module is positioned at a location corresponding to a radial distance at which the magnetic substance disposed adjacent to the tag of the test platform is positioned.

22. The method according to claim 19, wherein the test platform includes a magnetic substance disposed adjacent to the reference material, the detection module includes a magnet for applying an attraction force to the magnetic substance so that the magnetic substance is stopped at a location at which the reference material faces the light receiver, and the moving the detection module in the radial direction comprises moving the detection module in the radial direction until the magnet of the detection module arrives at a location corresponding to a radial distance at which the magnetic substance disposed adjacent to the reference material of the test platform is positioned.

23. The method according to claim 22, wherein the rotating the test platform comprises rotating the test platform so that the magnetic substance of the test platform faces the magnet of the detection module when the magnet of the detection module is positioned at a location corresponding to a radial distance at which the magnetic substance disposed adjacent to the reference material of the test platform is positioned.

24. The method according to claim 20, wherein the comparing the reference value to the result of the detection comprises:

moving the detection module in a radial direction with respect to the test platform until the light receiver of the detection module arrives at a location corresponding to a radial distance at which the reference material is positioned;

rotating the test platform until the reference material faces the light receiver; and receiving, in response to determining that the light receiver detects light passed through one or more colors printed on the reference material, the result of the detection from the light receiver, and comparing the reference value to the result of the detection.

25. The method according to claim 18, wherein the correcting the light receiver of the detection module comprises:

correcting, in response to determining that the result of the detection is not identical to the reference value, a detection condition of the light receiver such that the result of detection by the light receiver is identical to the reference value, and after the detection condition of the light receiver is corrected, controlling the light receiver to detect light passed through one or more colors printed on the reference material, and determining whether the result of the detection is identical to the reference value.

* * * * *